United States Patent [19]
Scholz et al.

[11] Patent Number: 5,976,610
[45] Date of Patent: *Nov. 2, 1999

[54] METHOD OF MAKING A LIGHT-WEIGHT ORTHOPEDIC CASTING ARTICLE

[75] Inventors: Matthew T. Scholz, Woodbury; Jason L. Edgar, Bloomington; Andrew J. Callinan, Robbinsdale; Dean A. Ersfeld, Maplewood; Worku A. Mindaye, Cottage Grove, all of Minn.

[73] Assignee: Minnesota Mining and Manufacturing Company, St. Paul, Minn.

[ * ] Notice: This patent is subject to a terminal disclaimer.

[21] Appl. No.: 08/963,854

[22] Filed: Nov. 4, 1997

Related U.S. Application Data

[62] Division of application No. 08/461,668, Jun. 5, 1995, Pat. No. 5,716,661, which is a division of application No. 08/320,917, Oct. 11, 1994, which is a continuation-in-part of application No. PCT/US94/02950, Mar. 17, 1994, which is a continuation-in-part of application No. 08/184,657, Jan. 21, 1994, abandoned, which is a continuation-in-part of application No. 08/049,007, Apr. 16, 1993, abandoned.

[30]     Foreign Application Priority Data

Mar. 17, 1994 [JP] Japan ..................... 6-913920
Apr. 8, 1994 [MX] Mexico ..................... 942584
Oct. 11, 1994 [WO] WIPO ............... PCT/US94/11508

[51] Int. Cl.⁶ .............. A61L 15/10; B05D 1/28; B05D 3/12; B05D 7/04
[52] U.S. Cl. .................. 427/2.31; 427/194; 427/358; 427/389.9; 427/412; 427/428
[58] Field of Search ................. 427/2.31, 389.9, 427/412, 428, 194, 180, 189, 358

[56]           References Cited

U.S. PATENT DOCUMENTS

| | | | |
|---|---|---|---|
| 3,630,194 | 12/1971 | Boardman | 128/90 |
| 3,669,708 | 6/1972 | Reber et al. | 117/33 |
| 3,908,644 | 9/1975 | Neinart et al. | 128/90 |
| 3,932,526 | 1/1976 | Koshar | 260/607 A |
| 3,972,323 | 8/1976 | Boricheski | 128/91 R |
| 4,038,238 | 7/1977 | Cravens | 524/792 |
| 4,085,180 | 4/1978 | Stoffey | 264/128 |
| 4,131,114 | 12/1978 | Kirkpatrick et al. | 128/90 |
| 4,306,548 | 12/1981 | Cogliano | 128/90 |
| 4,411,262 | 10/1983 | von Bonin et al. | 128/90 |
| 4,454,873 | 6/1984 | Laufenberg et al. | 128/90 |
| 4,468,254 | 8/1984 | Yokoyama et al. | 524/478 |
| 4,473,671 | 9/1984 | Green | 523/105 |
| 4,483,333 | 11/1984 | Wartman | 128/90 |
| 4,502,479 | 3/1985 | Garwood et al. | 128/90 |
| 4,539,345 | 9/1985 | Hansen | 523/219 |
| 4,609,578 | 9/1986 | Reed | 428/76 |
| 4,667,661 | 5/1987 | Scholz et al. | 128/90 |
| 4,668,563 | 5/1987 | Buese et al. | 428/230 |
| 4,683,877 | 8/1987 | Ersfeld et al. | 128/90 |
| 4,705,840 | 11/1987 | Buckanin | 528/53 |
| 4,841,958 | 6/1989 | Ersfeld et al. | 128/90 |
| 4,888,225 | 12/1989 | Sandvig et al. | 428/71 |
| 4,899,738 | 2/1990 | Parker | 128/90 |
| 4,947,839 | 8/1990 | Clark et al. | 128/90 |
| 4,996,979 | 3/1991 | Grim et al. | 128/89 R |
| 5,014,403 | 5/1991 | Buese | 28/170 |
| 5,027,803 | 7/1991 | Scholz et al. | 128/89 R |
| 5,087,643 | 2/1992 | Truong | 523/176 |
| 5,151,315 | 9/1992 | Ponnet | 428/212 |
| 5,228,164 | 7/1993 | Graf et al. | 12/133 R |
| 5,346,939 | 9/1994 | Moren et al. | 524/176 |
| 5,353,486 | 10/1994 | Schmidt et al. | 28/167 |
| 5,354,259 | 10/1994 | Scholz et al. | 602/8 |
| 5,364,693 | 11/1994 | Moren et al. | 428/263 |
| 5,382,445 | 1/1995 | Yasis | 427/2.31 |
| 5,405,643 | 4/1995 | Scholz | 427/2.31 |
| 5,423,735 | 6/1995 | Callinan et al. | 602/8 |
| 5,593,628 | 1/1997 | Scholz et al. | 156/167 |
| 5,603,691 | 2/1997 | Scholz et al. | 602/8 |
| 5,716,661 | 2/1998 | Scholz et al. | 427/2.31 |

FOREIGN PATENT DOCUMENTS

| | | |
|---|---|---|
| 0 407 056 | 9/1991 | European Pat. Off. . |
| 1050158 | of 0000 | France . |
| WO 90/14060 | 11/1990 | WIPO . |
| WO 94/03211 | 2/1994 | WIPO . |

OTHER PUBLICATIONS

European Search Report for EP97 116349, Jan. 1998.
C.R. Noller, *Chemistry of Organic Compounds*, Ch. 6, pp. 121–122 (1957) No Month.

*Primary Examiner*—Diana Dudash
*Attorney, Agent, or Firm*—F. Andrew Ubel

[57]           ABSTRACT

The present invention provides an article comprising a curable resin and a filler associated with the resin. The incorporation of fillers into the casting materials of the present invention adds substantially to the strength of the cured casting material as well as to the handling properties of the uncured casting tape or bandage. The incorporation of fillers into the casting materials of the present invention also imparts air and vapor porosity to the cured casting materials. If desired articles of the present invention may also incorporate fibers (either individually, bundled, or in the form of a light-weight scrim) to provide increased cohesiveness to the uncured article. Extremely moldable casting tapes are also provided which comprise a highly-filled composite material coated on a light-weight scrim. The casting tapes of this embodiment handle like traditional plaster of Paris casts yet cure to a weight-bearing cast in less than one hour. The ratio of the volume of filler to volume of prepolymer or resin is >0.40.

19 Claims, 4 Drawing Sheets

METHOD OF MAKING A LIGHT-WEIGHT ORTHOPEDIC CASTING ARTICLE

This is a division of U.S. patent application Ser. No. 08/461,668, filed Jun. 5, 1995, now U.S. Pat. No. 5,716,661, which is a division of U.S. patent application Ser. No. 08/320,917 filed Oct. 11, 1994, pending, which is a continuation-in-part of PCT Patent Application US94/02950 filed Mar. 17, 1994 which is a continuation-in-part of U.S. patent application Ser. No. 08/184,657, abandoned, filed Jan. 21, 1994 which is a continuation-in-part of U.S. patent application Ser. No. 08/049,007 filed Apr. 16, 1993, abandoned, which are herein incorporated by reference.

FIELD OF THE INVENTION

This invention relates to novel curable or thermoplastic composites useful in orthopedic casting applications.

BACKGROUND OF THE INVENTION

Many different orthopedic casting materials have been developed for use in the immobilization of broken or otherwise injured body limbs. Some of the first casting materials developed for this purpose involved the use of plaster of Paris bandages consisting of a mesh fabric (e.g., cotton gauze) with plaster (e.g., calcium sulfate hemihydrate) incorporated into the openings and onto the surface of the mesh fabric.

Plaster of Paris casts, however, have a number of attendant disadvantages, including a low strength-to-weight ratio, resulting in a finished cast which is very heavy and bulky. In addition, plaster of Paris casts develop their strength over a relatively long period of time, thus making it necessary to avoid weight bearing situations for up to 24 to 48 hours. Furthermore, plaster of Paris casts typically disintegrate in water, thus making it necessary to avoid bathing, showering, or other activities involving contact with water.

A significant advancement in the art was achieved when polyisocyanate prepolymers were found to be useful in formulating a resin for orthopedic casting materials, as disclosed, for example, in U.S. Pat. Nos. 4,502,479 (Garwood et al.), 4,441,262 (Von Bonin et al.) and 4,667,661 (Scholz et al). U.S. Pat. No. 4,502,479 sets forth an orthopedic casting material comprising a knit fabric which is made from a high modulus fiber (e.g., fiberglass) impregnated with a polyisocyanate prepolymer resin such as polyurethane. Orthopedic casting materials made in accordance with U.S. Pat. Nos. 4,502,479 and 4,667,661 provide significant advancement over the plaster of Paris orthopedic casts, including a higher strength-to-weight ratio and greater air permeability. However, such orthopedic casting materials tend not to permit tactile manipulation or palpation of the fine bone structure beneath the cast to the extent possible when applying a plaster of Paris cast. In this regard, knit fiberglass materials are not as compressible as plaster, and tend to mask the fine structure of the bone as the cast is applied, e.g., the care provider may be limited in "feeling" the bone during immobilization of the fracture. Although fiberglass fabrics are somewhat radiolucent, they sometimes tend to mask the underlying fine bone structure to x-ray penetration. Oftentimes a fine mesh or a "shadow" can be seen on the x-ray image. This mesh, corresponding to the knitted fiberglass backing, obstructs the penetration of the x-rays and thereby obscures the fine detail of the underlying bone on the x-ray image. In addition, knitted fiberglass backings, when cured, are quite rough compared to plaster of Paris casts and often produce casts with sharp edges. The surface roughness and/or sharp edges can cause skin abrasions, snag clothing, and damage household fixtures (e.g., a toilet seat can be easily damaged when a rough fiberglass cast is rubbed against it as a person sits down).

Fiberglass backings have further disadvantages. Most, if not all, commercially available fiberglass casting bandages are comprised of filaments with diameters much larger than 3.5 microns ($\mu$m). While 3.5 $\mu$m fibers are considered by the scientific community to be non-respirable, there exists a sizable number of customers that have become concerned about the inhalation of fiberglass dust generated during cast removal. Moreover, orthopedic casting materials involving knit fabrics such as fiberglass are somewhat expensive, and may be cost prohibitive for some users.

An example of an orthopedic bandage using a polyester fabric which is not a knitted fabric is disclosed in U.S. Pat. No. 3,972,323 (Boricheski). However, the orthopedic bandage disclosed in U.S. Pat. No. 3,972,323 involves the use of plaster of Paris, and thus is subject to the disadvantages outlined for plaster of Paris orthopedic casts, including an inferior strength-to-weight ratio and poor air permeability. A second example of an orthopedic bandage using a polyester fabric which is not a knitted fabric is disclosed in U.S. Pat. No. 4,841,958 (Ersfeld et al.). However, the polyester fabric backing disclosed in U.S. Pat. No. 4,841,958 causes the cast to have a somewhat lower strength and a lower rigidity than fiberglass casts. Thus, these casting materials (when used with an ordinary resin system) require more layers of casting tape to achieve a weight bearing orthopedic cast.

A cast material comprising a filled thermoplastic crystalline solid polyurethane is disclosed in U.S. Pat. No. 4,473,671 (Green). In use, the orthopedic cast material is warmed to a sufficiently high temperature to cause the polymer therein to become soft enough to deform. The orthopedic cast material is molded to conform to the surface shape of the effected portion of the body and then is cooled to room temperature. The filler of the casting material comprises a blend of 20% to 60% by weight of calcium metasilicate fibers and from 40% to 80% by weight silica particles. Thermoplastic polymers have also previously been employed in splinting products but have found limited acceptability due to their low porosity. U.S. Pat. No. 4,454,873 (Laufenberg) discloses an orthopedic cast material comprising a thermoplastic material and a coating of (poly) ethylene oxide. The coating is said to prevent adherence of adjacent convolutions of the cast material when it is molten.

A tubular casting system comprising an integral tubular bulky knitted substrate carrying a hardenable resin and an undercast padding layer is disclosed in International Patent Application No. WO 90/14060 (Blott et al.). A water soluble but resin impervious barrier layer intermediate to the padding and resin bearing layers is discussed.

From the foregoing, it will be appreciated that what is needed in the art is an orthopedic casting material which has both the advantages of plaster of Paris, e.g., good moldability and palpability of the fine bone structure, and the advantages of non-plaster of Paris materials, e.g., good strength-to-weight ratio, fast strength build-up, and preferably good air permeability. In this regard it would be significant advancement in the art to provide such a combination of advantages without actually using plaster of Paris, thereby avoiding the inherent disadvantages of plaster of Paris outlined herein. It would be a further advancement in the art to provide such non-plaster of Paris orthopedic casting materials which have as good or better properties than the knitted orthopedic casting materials of the prior art, and which can be made to be significantly less expensive, and therefore less cost prohibitive, than prior art orthopedic casting materials employing knitted fabrics such as fiberglass knits. Such orthopedic casting materials and methods for preparing the same are disclosed and claimed herein.

RELATED APPLICATIONS

Of related interest are the following U.S. patent applications, filed on Apr. 16, 1993 by the assignee of this invention: Process and Novel Casting Materials, Ser. No. 08/048,891; Water Soluble Films Used in Synthetic Casting Tapes, Ser. No. 08/048,738; and Novel Casting Tapes and Resins and Processes Therefor, Ser. No. 08/048,656 which are herein incorporated by reference. Also of related interest are the following U.S. patent applications, filed on Jan. 25, 1993 by the assignee of this invention: Water Curable Resin Compositions—Serial No. 08/008,743, now U.S. Pat. No. 5,346,939; Orthopedic Support Materials and Method—Ser. No. 08/008,678, now U.S. Pat. No. 5,346,939; and Microfiber Fillers for Orthopedic Casting Tapes—Ser. No. 08/008,755, now U.S. Pat. No. 5,354,259 which are herein incorporated by reference.

SUMMARY OF THE INVENTION

In one embodiment, this invention relates to novel curable or thermoplastic composites, useful in orthopedic casting applications, which offer the moldability and conformability of plaster of Paris with the strength of synthetic fiberglass casting materials. This embodiment provides a composite article comprising a binder (e.g., a curable resin) and a filler which may be used as a "scrimless" orthopedic casting tape. Preferred materials comprise highly filled resin systems and optionally incorporate a light-weight mesh fabric for added web integrity. The incorporation of fillers into the casting materials of this embodiment adds substantially to the strength of the cured casting material as well as to the handling properties of the uncured casting tape or bandage. The incorporation of fillers into the casting materials of this embodiment also imparts air and vapor porosity to the cured casting materials. Therefore, the disadvantages of fiberglass backings (such as limited conformability) can be avoided while maintaining the necessary high strength and high rigidity upon cure. If desired, articles of this embodiment may also incorporate fibers (either as individual randomly oriented fibers, as fiber bundles, or in the form of a light-weight scrim) to provide increased cohesiveness to the uncured article.

In a presently preferred embodiment, this invention relates to novel curable casting articles which offer the moldability and conformability of plaster of Paris, yet which cure quickly to form a strong article. In this embodiment, the casting article is provided in the form of a composite sheet comprising a mixture of a water curable resin and a filler which is coated on a scrim, preferably a light-weight scrim. The filler loading by volume is preferably quite high relative to the volume of liquid resin, thereby enabling the mixture to be coated even on relatively light-weight scrims without "pooling". Once activated, the casting article may be wrapped about a body part and cured. This embodiment exhibits exceptionally good moldability and smoothness while retaining the fast strength build-up of conventional synthetic fiberglass casting materials.

BRIEF DESCRIPTION OF THE DRAWINGS

The invention may be more clearly understood by reference to the drawings, wherein:

In FIG. 1 a portion of a composite article 1 is illustrated, wherein the composite article consists of spherical filler particles 2, resin domains 3, and empty void spaces 4. FIG. 2 depicts a similar composite article 5, wherein the filler particles 6 are irregularly shaped. FIG. 3 shows a partially unwound roll of casting tape 7, comprising a composite casting material 8, and a fugitive water-soluble liner 9. FIGS. 3A and 3B show a perspective view of a casting tape wherein the casting material 8 is in the form of a sheet which has a fugitive water-soluble liner 9 adjacent to both its major surfaces. FIG. 4 shows a perspective view of a roll of casting tape 11 which is enclosed in a water-soluble bag 10. FIG. 5 shows a partially unwound roll of casting tape 20, comprising a composite casting material 24, and two layers of a light-weight scrim or web 22. Also shown in FIG. 5 are a plurality of surface irregularities 26 which cross the width of the tape and facilitate transport of water to the center portion of the roll when the roll is immersed in water. FIG. 6 shows a partially unwound roll of casting tape 30, comprising a plurality of strips of a composite casting material 34, and two layers of a light-weight scrim or web 32. Also shown in FIG. 6 are gaps 38 between the adjacent strips of composite material. The gaps facilitate transport of water to the center portion of the roll when the roll is immersed in water. FIGS. 7a and 7b show a presently preferred casting tape 40 of the present invention comprising a composite mixture 42 of a curable resin and filler coated on a light-weight scrim 44. FIG. 7b shows a cross-section of the tape 40 of FIG. 7a taken along line B—B. Notably, this cross-section, although not drawn to scale, illustrates a tape 40 having a relatively thick coating of composite mixture (comprising resin 46 and filler 48) on a relatively thin, light-weight scrim 44. The coating is able to be easily molded during application and thereby conform to the desired shape.

DETAILED DESCRIPTION OF THE INVENTION

In one embodiment, the present invention relates to porous orthopedic casting materials and methods for preparing and using such orthopedic casting materials, wherein the materials comprise a binder (e.g., a curable resin) which is associated with a filler. In particular, the resins and fillers employed in the present invention have important characteristics and physical properties which allow the materials to possess sufficient strength for use as an orthopedic casting material even without the use of a separate scrim. The materials also have the necessary porosity and radiolucency for use as an orthopedic casting material and possess improved tactile manipulability, moldability, and palpability. At the same time, the orthopedic casting materials of this embodiment are relatively inexpensive, thus providing a more economical alternative to the orthopedic casting materials presently known in the art which often employ knitted fiberglass fabrics.

Figure 1:
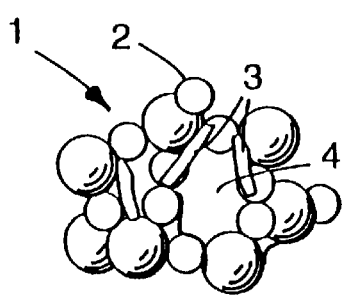
FIG. 1 shows a schematic representation of a composite structure comprising spherical particles, resin associated with said particles, and void spaces.
Figure 2:
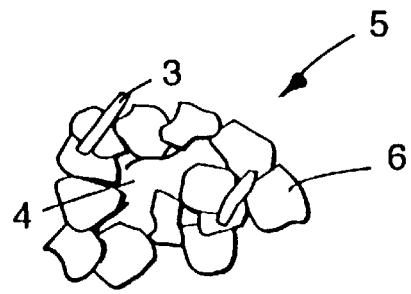
FIG. 2 shows a schematic representation of a composite structure comprising irregularly shaped particles, resin associated with said particles, and void spaces.
Figure 3:
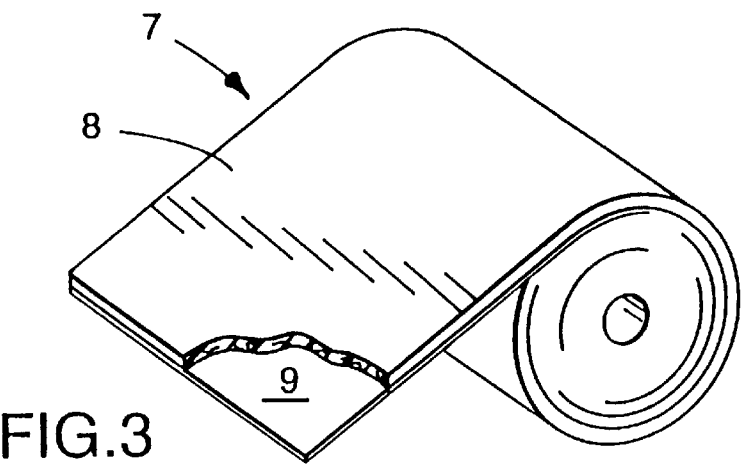
FIG. 3 shows a perspective view of a roll form casting tape comprising a composite, casting material and a water-soluble liner film.
Figure 4:
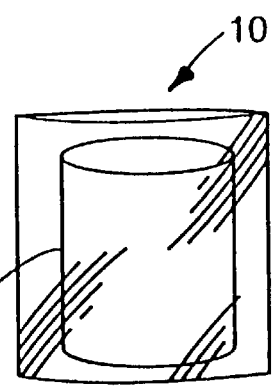
FIG. 4 shows a perspective view of a roll of casting tape in a water soluble bag.
Figure 3A:
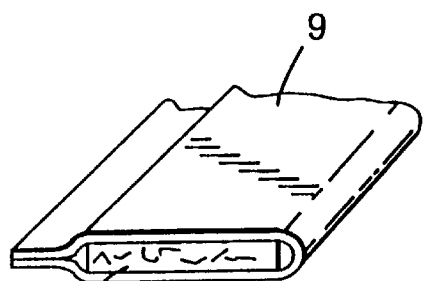
FIGS. 3A and 3B show a perspective view of a casting tape comprising a composite casting material and a water-soluble liner film.
Figure 3B:
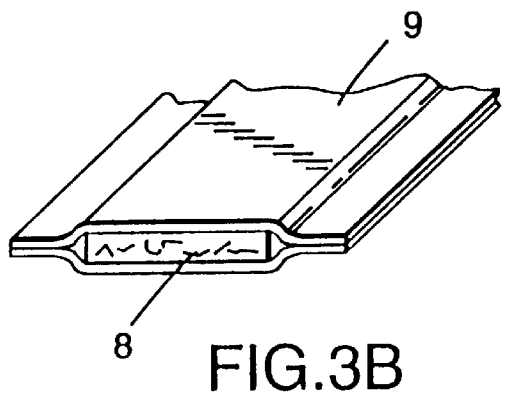
Figure 5:
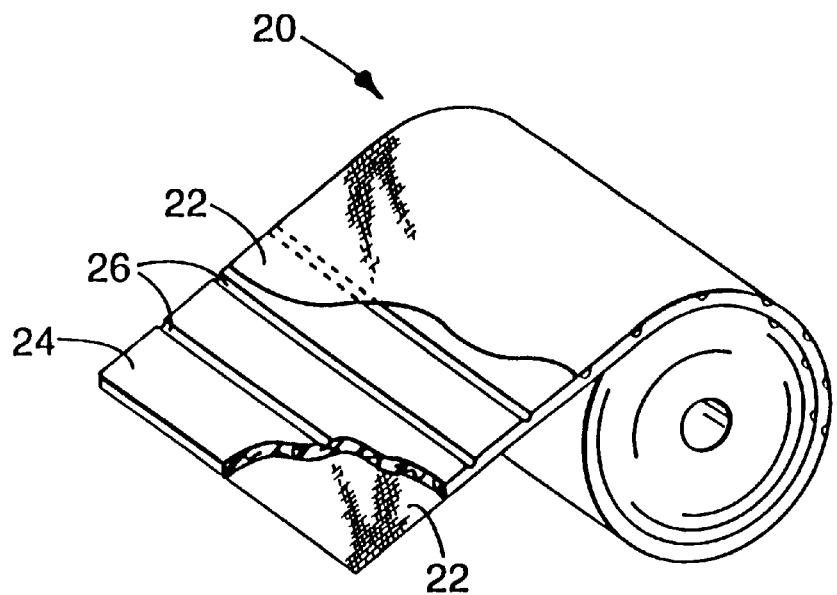
FIG. 5 shows a perspective view of a roll form casting tape comprising a composite casting material sandwiched between two layers of a light-weight scrim material.

The porous materials of this embodiment may be supplied in tape, splint, tubular and various laminate forms. The porous materials of this embodiment are, in general, characterized as high filler content materials which are held together by a "binder" component (i.e., either a curable resin or a thermoplastic polymer). Preferably the filler loading is high enough and the binder content low enough that the composite product is porous to air and moisture. While not intending to be bound by theory, it is presently believed that the binder serves to bond the particles together at point locations as depicted in FIGS. 1 and 2. Voids between the particles are presently believed to provide porosity to the cured composite. As used herein, a cast which has sufficient porosity to allow moisture vapors produced by the skin to freely escape through the cured cast is said to be "breathable" or to "breathe."

In another embodiment, the present invention relates to orthopedic casting tapes comprising a composite mixture of a curable resin and a filler coated on a preferably lightweight scrim. When uncured, the resin and filler composite mixture has important characteristics and physical properties (e.g., rheological properties) which allow the mixture to possess sufficient integrity for use as a coating on a lightweight scrim. Casting tapes of this embodiment exhibit exceptional smoothness during application and handle in a manner similar to plaster of Paris. When cured, the materials also have the necessary strength for use as an orthopedic casting material and during curing possess improved tactile manipulability, moldability, smoothability and palpability.

Conformability of current synthetic casting materials is often limited by the fabric backing (i.e., "scrim") used to carry the composite. Since the presently preferred casting materials of the present invention have only a very light fabric backing or no fabric backing the conformability is limited primarily by the rheology of the composite (i.e., resin and filler mixture). Combination of suitable fillers and resins of the present invention will provide a product having exceptional moldability. Casting materials which exceed the moldability of traditional Plaster-of-Paris materials have been obtained. The finished cast or splint of the present invention is also preferably strong, light-weight, radiolucent, and porous.

Suitable fillers for use in the present invention comprise inorganic or organic, particulate or fibrous materials which are insoluble in the curable resin. Filler morphologies may include spheres, bubbles, expandable bubbles, particulate materials, filaments, microfibers, flakes and platelet type materials, as well as combinations of these. The fillers may have a solid, porous, or hollow structure. Preferred fillers are light-weight and of a shape which does not pack particularly well thereby preferably ensuring sufficient void volume to render the composite sufficiently porous to moisture vapor.

More preferably, the fillers have a generally spherical shape and the composite is porous to moisture vapors. Most preferably, the casting products of the present invention are as porous as traditional fiberglass knit casting tapes.

Suitable inorganic filler materials include: glass, amorphous and crystalline silica ($SiO_2$), soda lime borosilicate, amorphous sodium/potassium/aluminum silicate glass, alumina (aluminum oxide), iron oxides, calcium metasilicate, calcium carbonate, calcium sulfate (in either a particulate or microfiber form), kaolin, mica, talc, barium sulfate, boron fibers, carbon fibers, glass fibers, ground glass fibers, flake glass, metallic fibers, feldspar, barium ferrite, titanium oxide, ceramics and the like. Preferred inorganic filler materials include glass and ceramic bubbles such as: Scotchlite™ brand glass bubbles H50/10000 EPX, H50/10000 (acid washed), K-46, and S60/10000 (available from 3M); Extendosphere™ brand SG, CG, SF-12 (available from PQ Corp.); Zeeosphere™ brand 200, 400, 600, 800, and 850 (available from 3M); Zeolite™ W1000, W1012, W1300, W1600, G3400, and G3500 (available from 3M); Dicaperl™ brand HP-900 and HP-920 (available from Grefco) and Sil-Cell™ brand Sil-35/34, Sil-32, Sil-42, and Sil-43 (available from Silbrico Corp., Hodgkins, Ill. 60525). Dicaperl™ brand HP-820, HP-720, HP-520, HP-220, HP-120, HP-900, HP-920, CS-10-400, CS-10-200, CS-10-125, CSM-10-300, and CSM-10-150 (available from Grefco, Torrance, Calif.), and ceramic particles such as Ceramcel™ (in sizes from 1.5 mm to 5 mm and available from Microcel Tech. Inc.) may also be suitable, particularly when blended with other fillers. Colored pigment fillers are also suitable. Blends of these fillers may also be suitable.

Suitable organic fillers include fillers comprised of thermoplastic or thermoset organic materials or both as well as composite filler materials comprising the afore-mentioned organic materials as matrix and inorganic micro-inclusions dispersed therein. Suitable organic fillers are insoluble in the curable resin. Suitable thermoplastic filler materials include polyolefins such as Primax brand UH-1080, UH-1060 and UH-1250 (available from Air Products & Chemicals—Allentown, Pa.), polyesters (e.g., poly(ethylene terephthalate), hereinafter referred to as "PET"), polyamides, polyimides, polyacrylates, polycarbonate, polyurethane and the like including copolymers of the afore-mentioned materials. Suitable thermoplastic filler materials also include expandable bubbles such as Expancel 461 DE 20 microspheres (available from Nobel Industries). Suitable thermoset filler materials include epoxies, aldehyde condensation products (e.g., Ucar Thermoset microballoons BJO-0950, BJO-0820, BJO-0900, BJO-0840, BJO-09300 available from Union Carbide, Danbury Conn.), acrylates, and methacrylates. Preferred organic filler materials include polyethylene microspheres (available from Air Products & Chemicals—Allentown, Pa.).

Preferred particulate fillers have an average particle diameter between 5 and 500 μm, more preferably the particulate fillers have an average particle diameter between 20 and 200 μm, most preferably the particulate fillers have an average particle diameter between 30 and 120 μm. A used herein, "average particle diameter" is defined as the diameter of a sphere of the same volume as the particle.

Microfibers may be added to the resin to enhance web integrity or composite strength. Preferred fibers for use in the present invention have an average length between 25 and 5,000 μm, more preferably the fibers have an average length between 30 and 1,000 μm, most preferably the fibers have an average length between 30 and 500 μm. Microfiber fillers such as those described in U.S. patent application No.

08/008,751, which is herein incorporated by reference, may also be useful alone or in combination with other particulate fillers or fibers.

Preferred fillers for use with isocyanate functional polyurethane prepolymers systems include: Scotchlite™ brand glass bubbles H50/10000 EPX, H50/10000 (acid washed), and S60/10000; Sil-Cell™ brand Sil-35/34, Sil-32, Sil-42, and Sil-43; Primax™ UH-1080, UH-1060 and UH-1250; and Dicaperl HP-820, HP-720, HP-520, HP-220, HP-120, HP900, HP920, CS-10-400, CS-10-200, CS-10-125, CSM-10-300,and CSM-10-150. Beneficial results have been demonstrated using a combination of spherical fillers and a fiber such as 1.5 denier×19.05 mm long PET fibers (available from Minifibers—Code No. 6 1575).

Suitable concentrations of filler in the resin (i.e., "filler loading") will vary depending on the bulk density of the filler, the specific gravity of the filler and particular resin employed, and the desired porosity and handling property of the composite. As used herein, "specific gravity" refers to the ratio of the density of a substance to the density of a reference substance. For solids and liquids the reference substance is water (density=1 g/cc), therefore the specific gravity of a solid or liquid is numerically equal to its density. The specific gravity of the filler particles is preferably less than 3, more preferably less than about 2 and most preferably less than 1. A suitable filler loading is determined by selecting a level which is sufficiently high to ensure adequate strength (and preferably good porosity) but not so high that the composite easily fractures or crumbles or is otherwise difficult to apply.

One method of characterizing the porosity of a composite is to measure the volume fraction of void space in the composite material (hereinafter referred to as the composite's "void volume"). The void volume of a composite material is the unoccupied space of the composite which is accessible to the transport of air or water vapor. The void volume of a composite material may be measured as described in Example 14. For example, spaces which are filled with a gas (e.g., air or $CO_2$) and which are accessible to the transport of air or water vapor would be included in the void volume of the composite. The void volume may be conveniently expressed as a percentage of the composite's total volume. For composites which include components that are themselves porous (e.g., the composite comprises a porous filler), the void volume of the porous component should be included in the total void volume of the composite provided the component's voids are accessible to the transport of air or water vapor. For samples which exhibit resin foaming during cure (such as an isocyanate functional resin system) the void volume should be calculated by measuring the volume uptake of an inert solvent of low surface tension as described in Example 14. An inert solvent, as used in this test, is a solvent which does not appreciably swell or dissolve the cured composite. Isopropyl alcohol is a suitable inert solvent for most isocyanate functional resins systems. It is believed that resin foaming may create closed cell voids which are not accessible to the transport of air or water vapor and would not be included by the test described in Example 14. Notably, resin foaming may create open cell voids at the surface of the composite and closed cell voids throughout the material. Care should be taken when measuring void volume to ensure that the voids are accessible to the transport of air or water from either surface of the composite (i.e., that the solvent penetrates the whole thickness).

An important characteristic of preferred casting materials is a high strength to weight ratio. In order to ensure a light weight composite, preferred fillers have a bulk density of less than 1.0 $g/cm^3$, more preferred fillers have a bulk density of less than 0.75 $g/cm^3$ and most preferred fillers have a bulk density of less than about 0.6 $g/cm^3$. A filler's "bulk" density or "apparent" density, as used herein, is determined by weighing the amount of filler which occupies a unit volume. To make this determination a 10 gm sample of filler is placed into a suitable sized graduated cylinder (e.g., about 25 $cm^3$) so that the filler occupies about half its height. The cylinder is then gently shaken side-to-side for 5 minutes to allow settling. The volume of filler is then read from the graduations on the cylinder side.

The articles of the present invention may also be provided as a tape or sheet form having a plurality of macroscopic holes through its thickness. A "macroscopic hole," as used herein, is a hole which extends through the thickness of the tape. In contrast, the previously mentioned "void volume" or "pores" are characterized as void spaces surrounding individual particles of the composite material. The void spaces are dispersed throughout the composite but, while providing a path through which water vapor may escape, do not form foraminous "holes" through the thickness of the tape. As a further guide to differentiating a "pore" from a "hole" it is presently believed that a pore has a diameter less than 1000 $\mu$m, while a hole has a diameter of 1000 $\mu$m or more.

The articles of the present invention may also be provided as a tape or sheet form having a plurality of macroscopic surface irregularities (e.g., out-of-plane bumps or depressions) which run transverse across the tape or sheet and extend to or near the edge of the sheet and limit tight contact of adjacent layers of a roll. These surface irregularities facilitate migration of water to the center portion of a roll of tape, e.g., when curing is being initiated. Preferably, these surface irregularities are easily smoothed out when the initiated tape is molded into a cast.

Preferred porous composites of the present invention contain between 30 and percent by volume filler, more preferably, between 40 and 75 percent by volume filler, and most preferably, between 50 and 70 percent by volume filler. Preferred porous composites of the present invention have between 8 and 40 volume percent resin, more preferably, between 10 and 30 volume percent resin, and most preferably, between 12 and 25 volume percent resin. Preferred porous composites of the present invention have at least 7 percent void volume, more preferably, at least 10 percent void volume, and most preferably, at least 12 percent void volume.

Preferred orthopedic casting tapes which comprise a composite mixture of a curable resin and a filler coated on a light-weight scrim contain between 30 and 85 percent by volume filler, more preferably, between 40 and 75 percent by volume filler, and most preferably, between 50 and 70 percent by volume filler. Preferred orthopedic casting tapes which comprise a composite mixture of a curable resin and a filler coated on a light-weight scrim have between 8 and 40 volume percent resin, more preferably, between 10 and 30 volume percent resin, and most preferably, between 12 and 25 volume percent resin. It is desirable that the rheology of the composite mixture be adjusted so that the composite mixture can be easily coated on the light weight scrim at the desired coating weight, yet does not "pool" during storage. Surprisingly, it has been discovered that such a mixture can be achieved by thoroughly mixing a filler into a resin system, wherein the resin system comprises a blend of prepolymer materials. The composite mixture (comprising filler, and resin components) is then coated onto the light-weight scrim before the resin system has developed its final molecular weight (and hence its viscosity has not built up fully). After the composite mixture has been coated on the scrim, the resin builds up additional viscosity due to a reaction between the prepolymer components. Thus, the composite mixture achieves a final storage rheology which resists pooling. It has been discovered that the volume ratio of filler to resin provides an important indication of a composite material's likely rheological properties. As the volume fraction of filler to resin is increased the composite is likely to become increasingly viscous and, consequently, less likely to pool. Preferred composite mixtures for coating on light-weight weight scrims have a volume ratio of filler to resin ($V_f/V_r$) of at least 0.4, more preferably at least 0.6, and most preferably at least 0.8.

Preferred fillers for use with water curable resins also have very low moisture absorbency. Preferably the filler contains less than 4% by weight absorbed water, more preferably the filler contains less than 1% by weight absorbed water and most preferably the filler contains less than 0.5% by weight absorbed water. The amount of absorbed water in a filler sample may be determined by heating the filler in an oven and measuring the sample's weight loss. For fillers that have a high amount of moisture one may preferably dry the filler prior to incorporation into the composite.

The shelf stability of the composite mixture is an important consideration when selecting suitable filler and resin combinations. Shelf stability refers to the ability of the finished product to resist degradation or significant increase in viscosity during normal storage conditions. For example, for products comprising isocyanate functional polyurethane prepolymers such standard storage conditions would include storage in a moisture free environment at 25° C. Notably, many commercially available fillers, such as glass bubbles, are basic in nature (i.e., alkali) and may cause undesirable side-reactions in isocyanate functional polyurethane prepolymers. These side reactions may cause the resin to harden prematurely or prevent hardening at all. Preferred fillers are chosen so as to not upset the shelf stability of the resin material. The shelf stability of a casting material preferably exceeds 1 year when stored at ambient temperature (i.e., 25° C.), more preferably the shelf stability of a casting material exceeds 3 years when stored at ambient temperature and most preferably the shelf stability of a casting material exceeds 5 years when stored at ambient temperature. The shelf stability of a casting material may also be tested at elevated temperature (49° C.) to predict ambient temperature stability. Preferred casting materials withstand four weeks at 49° C., more preferred casting materials withstand eight weeks at 49° C., and most preferred casting materials withstand twelve weeks at 49° C. When isocyanate functional polyurethane prepolymers systems are employed it is beneficial to ensure that the fillers are neither basic in nature nor contain basic impurities. Such basicity can result in side reactions (such as trimerization, allophonate formation, and biuret formation) with the isocyanate functional resin system which may limit the shelf stability of the product. Adverse effects of the basicity of the filler may be minimized by washing and/or neutralizing the filler with a suitable acid or by addition of an acid stabilizer to the resin.

If desired, the fillers may be surface treated using silanes, titanates, zirconates and the like to enhance resin bonding, ease of mixing, and compatibility. The surface treatment may be performed prior to incorporation of the filler into the resin or in-situ, i.e., the surface treatment agent may be incorporate into the resin for later reaction with the filler.

As previously mentioned, a curable resin may be employed as a binder. The curable-resin used in the casting material of the invention is preferably any curable resin which will satisfy the functional requirements of an orthopedic cast. Obviously, the resin must be nontoxic in the sense that it does not give off significant amounts of toxic vapors during curing which may be harmful to either the patient or the person applying the cast and also that it does not cause skin irritation either by chemical irritation or the generation of excessive heat during cure. Furthermore, the resin must be sufficiently reactive with the curing agent to insure rapid hardening of the cast once it is applied but not so reactive that it does not allow sufficient working time to apply and shape the cast. Initially, the casting material must be pliable and formable and should adhere to itself. Then in a short time following completion of cast application, it should become rigid or, at least, semi-rigid, and strong to support loads and stresses to which the cast is subjected by the activities of the wearer. Thus, the casting material must undergo a change of state from a viscoelastic condition (e.g., a moldable putty) to a solid condition in a matter of minutes.

In one embodiment, the resins are highly viscoelastic water-curable resins which resists "pooling", even when coated on a very light-weight scrim. In another embodiment, the resin, when mixed with the filler, forms a highly viscous mixture which resists "pooling", even when coated on a very light-weight scrim. As taught herein, many traditional non-viscoelastic resins may be modified to be highly viscoelastic (i.e., the resin's tan δ value is decreased) and therefore suitable for use in this invention. Presently preferred are urethane resins formed by the reaction of a polyisocyanate and a polyol such as those disclosed in U.S. Pat. No. 4,131,114. A number of classes of water-curable resins known in the art are suitable, including polyurethanes, cyanoacrylate esters, and, when combined with moisture sensitive catalysts, epoxy resins and prepolymers terminated at their ends with trialkoxy- or trihalo-silane groups. For example, U.S. Pat. No. 3,932,526 discloses that 1,1-bis (perfluoromethylsulfonyl)-2-aryl ethylenes cause epoxy resins containing traces of moisture to become polymerized.

Resin systems other that those which are water-curable may be used, although the use of water to activate the hardening of an orthopedic casting tape is most convenient, safe and familiar to orthopedic surgeons and medical casting personnel. Preferred resins are not appreciably dispersible in water. Resins such as those disclosed in U.S. Pat. No. 3,908,644 in which a bandage is impregnated with difunctional acrylates or methacrylates, such as the bis-methacrylate ester derived from the Condensation of glycidyl methacrylate and bisphenol A (4,4'-isopropylidenediphenol) are suitable. The resin is hardened upon wetting with solutions of a tertiary amine and an organic peroxide. Also, the water may contain a catalyst or initiator. For example, U.S. Pat. No. 3,630,194 proposes an orthopedic tape impregnated with acrylamide monomers whose polymerization is initiated by dipping the bandage in an aqueous solution of oxidizing and reducing agents (known in the art as a redox initiator system). The strength, rigidity and rate of hardening of such a bandage are subject to formulation variables as disclosed herein. The following disclosure relates primarily to the presently preferred embodiments of the invention wherein water-curable isocyanate-functional prepolymers or water reactive liquid organometallic compounds are employed as the curable resin.

Some presently more preferred resins for use in the present invention are water-curable, isocyanate-functional prepolymers. Suitable systems of this type are disclosed, for example, in U.S. Pat. No. 4,411,262, and in U.S. Pat. No.

4,502,479. Presently more preferred resin systems are disclosed in U.S. Pat. No. 4,667,661 and U.S. patent application Ser. No. 07/376,421 which is herein incorporated by reference. A water-curable isocyanate-functional prepolymer as used herein means a prepolymer derived from a polyisocyanate compound and a reactive hydrogen compound or oligomer (e.g., a "polyol"). As used herein, a reactive hydrogen compound is a compound having active hydrogen in accordance with the well known Zerevitinov test as described, for example, in Chemistry of Organic Compounds by Carl R. Noller, Chapter 6, pp. 121–122 (1957). The prepolymer has sufficient isocyanate-functionality to cure upon exposure to water, e.g., moisture vapor, or preferably liquid water.

It is presently preferred to employ a polyisocyanate prepolymer formed by the reaction of an isocyanate and a polyol. It is preferred to use an isocyanate which has low volatility such as diphenylmethane diisocyanate (MDI) rather than a more volatile material such as toluene diisocyanate (TDI). Suitable isocyanates include 2,4-toluene diisocyanate, 2,6-toluene diisocyanate, mixture of these isomers, 4,4'-diphenylmethane diisocyanate, 2,4'-diphenylmethane diisocyanate, mixtu isomers together with possible small quantities of 2,2'-diphenylmethane diisocyanate (typical of commercially available diphenylmethane diisocyanate), and aromatic polyisocyanates and their mixture such as are derived from phosgenation of the condensation product of aniline and formaldehyde. Typical polyols for use in the prepolymer system include polyalkylene oxides (e.g., polyethylene oxide and polybutylene oxide), polypropylene ether glycols (available from Arco Chemical under the trade name Arcol™ PPG and from BASF Wyandotte under the trade name Pluracol™), polytetramethylene ether glycols (Polymeg™ from the Quaker Oats Co. or Terathane™ from the Du Pont de Nemours, E.I., Co., Wilmington Del.), polycaprolactone diols Tone™ series of polyols from Union Carbide), and polyester polyols (hydroxyl terminated polyesters obtained from esterification of dicarboxylic acids and diols such as the Rucoflex™ polyols available from Ruco division, Hooker Chemical Co.). By using high molecular weight polyols, the rigidity of the cured resin can be reduced.

An example of a resin useful in the casting material of the invention uses an isocyanate known as Isonate™ 2143L available from the Dow Chemical Company (a mixture of di- and tri-isocyanates containing about 73% of MDI) and a polypropylene oxide polyol from Union Carbide known as Niax™ PPG725. To prolong the shelf life of the material, it is preferred to include from 0.01 to 1.0 percent by weight of benzoyl chloride or another suitable stabilizer (based on total resin weight).

The reactivity of the resin once it is exposed to the water curing agent can be controlled by the use of a suitable amount of proper catalyst. The reactivity must not be so great that: (1) a hard film quickly forms on the resin surface preventing further penetration of the water into the bulk of the resin; or (2) the cast becomes rigid before the application and shaping is complete. Good results have been achieved using 4-[2-[1-methyl-2-(4-morpholinyl)ethoxy]ethyl]-morpholine ("MEMPE") prepared as described in U.S. Pat. No. 4,705,840 and 2,2' dimorphiolinodiethyl ether ("DMDEE") prepared as described in U.S. Pat. No. 4,433,680, the disclosure of which are incorporated by reference, at a concentration of about 0.05 to about 5 percent by weight (based on total resin weight).

Foaming of the resin should be minimized since it may adversely impact the surface smoothness of the cast and may decrease the cast's overall strength; Foaming may occur, for example, when carbon dioxide is released as a result of water reacting with an isocyanate group. One way to minimize foaming is to reduce the concentration of isocyanate groups in the prepolymer. However, to have reactivity, workability, and ultimate strength, an adequate concentration of isocyanate groups is necessary. Although foaming is less at low resin contents, adequate resin content is required for desirable cast characteristics such as strength and resistance to peeling. A satisfactory method of minimizing foaming is to add a foam suppressor such as silicone Antifoam A (Dow Corning), or Anti-foam 1400 silicone fluid (Dow Corning) to the resin. It is especially preferred to use a silicone liquid such as Dow Corning Anti-foam 1400 at a concentration of about 0.05 to 1.0 percent by weight. Water-curable resins containing a stable dispersion of hydrophobic polmeric particles, such as disclosed in U.S. patent application Ser. No. 07/376,421 and laid open as European Published Patent Application EPO 0 407 056, may also be used to reduce foaming.

In addition lubricants may be added to the resins in accordance with U.S. Pat. No. 4,667,661 such that the casting materials exhibit reduced tack prior to and during cure and yet form a cast with acceptable strength and lamination strength. Suitable lubricants include: hydrophilic groups which are covalently bond to the resin system; additives which are incompatible with the curable resin including: a surfactant, a polymer comprised of a plurality of hydrophilic groups, and a polysiloxane; and combinations of the above. The lubricant may be used in conjunction with a separate fugitive liner if desired.

Also included as presently preferred resins in the instant invention are non-isocyanate resins such as water reactive liquid organometallic co resins are preferred as an alternative to isocyanate resin systems. Water-curable resin compositions suitable for use in an orthopedic cast consist of a water-reactive liquid organometallic compound and an organic polymer. The organometallic compound serves to reduce resin viscosity and is a compound of the formula $(R^1O)_x MR^2_{(y-x)}$ wherein: each $R^1$ is independently a $C_1$–$C_{100}$ hydrocarbon group, optionally interrupted in the backbone by 1–50 nonperoxide —O—, —S—, —C(O)—, or —N— groups; each $R^2$ is independently selected from the group consisting of hydrogen and a $C_1$–$C_{100}$ hydrocarbon group, optionally interrupted in the backbone by 1–50 nonperoxide —O—, —S—, —C(O)—, or —N— groups; x is an integer between 1 and y, inclusive; y is the valence of M; and M is boron, aluminum, silicon, or titanium. The organic polymer is either an addition polymer or a condensation polymer. Addition polymers are preferably utilized as the organic polymer constituent. Particularly useful addition polymers are those made from ethylenically unsaturated monomers. Commercially available monomers, from which such addition polymers can be formed, include but are not limited to, ethylene, isobutylene, 1-hexene, chlorotrifluoroethylene, vinylidene chloride, butadiene, isoprene, styrene, vinyl napthalene, ethyl acrylate, 2-ethylhexyl acrylate, tetrahydrofurfuryl acrylate, benzyl acrylate, poly(ethylene oxide) monoacrylate, heptafluorobutyl acrylate, acrylic acid, methyl methacrylate, 2-dimethylaminoethyl methacrylate, 3-methacryloxypropyltris(trimethylisiloxy) silane, isobutyl methacrylate, itaconic acid, vinyl acetate, vinyl stearate, N,N-dimethylacrylamide, tert-butyl acrylamide, acrylonitrile, isobutyl vin pyrrolidinone, vinyl azlactone, glycidyl methacrylate, 2-isocyanatoethyl methacrylate, maleic anhydride, vinyl triethoxysilane, vinyl tris(2- methoxyethoxy)silane, and 3-(trimethoxysilyl)propyl methacrylate. Polymers bearing hydrolzable functionality are preferred. An acidic or basic catalyst may be used to accelerate the water cure of these compositions. Strong acid catalysts are preferred. A more complete description of suitable water reactive liquid organometallic compounds is disclosed in pending U.S. patent application Ser. Nos. 08/008,678 now U.S. Pat. No. 5,364,693, and 08/008,743, now U.S. Pat. No. 5,386,939, which are herein incorporated by reference.

Also included as presently more preferred resins in the instant invention are the water curable alkoxy silane terminated oligomers disclosed in copending U.S. patent application "Novel Casting Tapes and Resins and Processes Therefor," Ser. No. 08/048,656, now U.S. Pat. No. 5,423,735. These resin compositions are preferably solventless.

Preferred resin compositions are stable, i.e., nonreactive, and do not significantly increase in viscosity at a temperature of less than about 40° C. In addition, preferred resin compositions are capable of curing upon exposure to water to form a hardened material at a temperature between about 10 to 100° C., preferably at a temperature between about 20 to 50° C. Preferred resin compositions include a low viscosity water-reactive alkoxysilane terminated polymer. The average alkoxysilane functionality is at least one and preferably at least two but may be as high as four. Each alkoxysilane group may have 2 or 3 hydrolyzable groups.

The water-reactive polymer having hydrolyzable terminal alkoxysilane groups is preferably a compound of the formula:

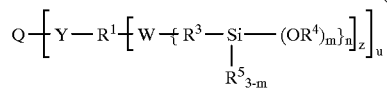
(Formula I)

wherein:

Q is a polyol residue;

W is —NHC(O)—X($R^2_{2,n-q}$)— to or —XC(O)NH—;

X=—O—, —$NR^8$, or —S—;

Y is —O—, —$NR^8$—, —S—, carbamylthio (—SC(O)NH—), carbamate (—OC(O)NH), or ureido, and N-substituted ureido (—NHC(O)NH—);

$R^1$ is a substituted or unsubstituted divalent bridging $C_1$–$C_{200}$ hydrocarbon group, optionally interrupted in the backbone by 1 to 50 nonperoxide —O—. —C(O)—, —S—, —$SO_2$—, —$NR^6$—, amide (—C(O)—NH—), ureido (—NH—C(O)—NH—), carbamate (—O—C(O)NH—), carbamylthio (—S—C(O)—NH—), unsubstituted allophanate (—NH—C(O)—N(C(O)—O—)—), unsubstituted and N-substituted biuret (—NH—C(O)—N(C(O)—N—)—), and N-substituted isocyanurate groups;

$R^2$ can be present (if n=1) or absent (if n=2) and is selected from the group consisting of a H and a substituted or unsubstituted $C_1$–$C_{20}$ hydrocarbon group, optionally interrupted in the backbone by 1 to 10 nonperoxide —O—, —C(O)—, —S—, —$SO_2$—, or —N($R^6$)— groups;

$R^3$ is a substituted or unsubstituted divalent bridging $C_1$–$C_{20}$ hydrocarbon group, optionally interrupted in the backbone by 1 to 5 nonperoxide —O—, —C(O)—, —S—, —$SO_2$—, or —N($R^6$)— to groups;

$R^4$ is a $C_1$ to $C_6$ hydrocarbon group or —N=C($R^7$)$_2$;

each $R^5$ and $R^7$ is independently a $C_1$ to $C_6$ hydrocarbon group;

$R^6$ is a $C_1$ to $C_6$ hydrocarbon group, or hydrogen;

$R^8$ is selected from the group consisting of a H and a substituted or unsubstituted $C_1$–$C_{20}$ hydrocarbon group, optionally interrupted in the backbone by 1 to 10 nonperoxide —O—, —C(O)—, —S—, —$SO_2$—, or —N($R^6$)— to groups;

n=1 to 2 and q=0 to 1, with the proviso that when X is N, n+q=1, and when X is S or O, n+q=2;

u=the functionality of the polyol residue=0 to 6, with the proviso that when u=0, the compound of Formula I is

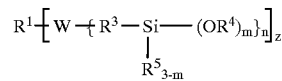
(Formula II)

m=2 to 3; and z=1 to 3.

Each "$R^3$—Si(O$R^4$)m" moiety can be the same or different. A preferred composition consists of toluene diisocyanate ("TDI") based pre-polymers end-capped with highly functionalized alkoxy silanes, such as bis(trimethoxysilylpropyl)amine.

For use in preparing alkoxy silane functionalized prepolymers, the currently preferred prepolymers precursors are those formed from polyols and reactive polyisocyanates with free NCO ranging from 1.9 to 9.0 percent and contain polyethylene glycol, polypropylene glycol, polytetramethylene glycol, polyester ether polyols and mixtures of these. The most preferred diisocyanate prepolymers are those containing polyethylene glycol, but include polyether polyols such as polytetramethylene glycol, polypropylene glycols, polybutylene glycols, and random or block copolymers of these, and polymer polyols such as those disclosed in U.S. patent application Ser. No. 07/376,421, now abandoned. Polyolefin polyols such as polybutadiene polyols and polyisoprene polyols may also be used as well as aromatic and aliphatic amine terminated "polyols" such as Jeffamine and Polamine materials, low molecular weight diols, thiols and the like. Mixtures and blends of these polyols may be useful. The preferred average polyol functionality is 1.8 to 3, more preferably 2 to 2.5 but polyols with functionalities as high as 4 or more may be useful.

For use in preparing alkoxy silane terminated prepolymers, the preferred polyisocyanates have differential reactivity, i.e. have at least one isocyanate group which is significantly more reactive than one or more isocyanate groups on the same molecule by a factor of 2 or more. The preferred isocyanates have a functionality of 2 to 3 while particularly preferred materials have functionalities of 2 to 2.3. The presently preferred isocyanate is TDI. Other aromatic isocyanates such as methylene diisocyanate ("MDI") and polyisocyanates based on condensation products of formaldehyde and aniline are potentially useful. Aliphatic isocyanates are useful and may be particularly preferred for applications where stability to ultraviolet light is of particular concern. Materials such as the trimer and biuret adducts of hexamethylene isocyanate ("HMDI"), methylene-bis-(4-cyclohexyl isocyanate), tetramethylxylene isocyanate ("TMXDI"), and xylene isocyanate could be used. Materials such as isophorone diisocyanate and the like are perhaps useful due to the differential reactivity of the isocyanate groups.

For use in preparing alkoxy silane terminated prepolymers, the preferred reactive silane of the present invention is bis(trimethoxysilylpropyl)amine, but other reactive silanes could be employed such as aminopropyltrimethoxysilane ("A-1110"), N-beta-(aminoethyl)-gamma-aminopropyl-trimethoxysilane ("A-1120"), gamma-mercaptopropyltrimethoxysilane ("Y-11167"), isocyanatopropyl trimethoxysilane, etc. Note that critical elements for a silane useful in the present invention are that it have: at least one active hydrogen group (except when W=—XC(O)NH—); at least one silane functionality; and at least 2 (and perferably 3) hydrolyzable groups in the silane (s).

Preferred silanes are trimethoxy- and triethoxy silanes but other trialkoxy, alkyldialkoxy, aryldialkoxy, and oximino silanes could be useful. These could also be reacted in various combinations and proportions with the TDI-based prepolymers to produce a wide range of average silane functionality (e.g., 2 to 4 or more).

Another important ingredient in the alkoxysilane terminated prepolymer resins is the catalyst for the moisture curable resin. It has been found that substituted guanidines and particularly N,N,N',N'-tetramethylguanidine ("TMG") is the preferred catalyst for these silane cure systems ensuring a sufficiently rapid hydrolysis of the alkoxysilane groups and subsequent condensation of the resulting silanols to form siloxane adducts. However, other basic tertiary amine catalysts could be used in this resin system such as 1,8-diazobicyclo[5,4,0]undecan-7-one ("DBU"), triethylamine, imidazoles, piperazines, etc. Acid catalysts such as sulfonic acids (including alkyl and perfluoroalkyl), carboxylic acids (including alkyl and perfluoroalkyl), phosphoric acids, boric acids and the like could also be employed with this resin system. Moreover, various metal catalysts such as ligands of tin, cobalt, bismuth, lead, zinc or titanium which are known to the art of silane cure could be used alone or in combination with the afore-mentioned catalysts in this resin system.

In one embodiment, the present invention provides porous composite materials with enhanced cohesiveness prior to hardening, most preferably without using a heavy fabric backing. Where a fabric backing may be deemed desirable, preferably only a light backing is used. Preferably, the resin system is highly cohesive to ensure the composite material will not crack as the product is molded and will support typical tensile forces which are placed on the uncured composite during the application procedure. When formulating the porous composite materials of the present invention one must strike a balance between the material's uncured "handling" properties (such as web cohesiveness, moldability, smoothability, resistance to pooling, etc.) and the material's cured physical properties (such as strength, porosity, surface smoothness, etc.). It is presently believed that the material's physical properties are substantially affected by the composite's filler to resin ratio. Unfortunately, as the filler to resin volume ratio is increased (thereby increasing cured composite porosity) the composite may become less cohesive or smoothable and more difficult to mold. For a given filler and resin system it may not be possible to formulate a composite which has both high strength and porosity and has good cohesiveness and/or smoothability in the uncured state. To alleviate this problem two different approaches are disclosed in the present invention. The first approach involves a modification to the resin component of the composite. This modification causes a decrease in the resin's tan δ and thereby increases the composite's cohesiveness. The second approach involves the incorporation of fibers into the composite (either as individual fibers or as a fabric scrim). The fibers provide enhanced cohesiveness to the composite and support some of the tensile forces which are placed on the uncured composite during application. A combination of these methods may be employed if desired.

In another embodiment, a casting tape is provided comprising a highly viscous mixture of resin and filler coated on a light-weight scrim. The coating on the casting tape, when activated, is highly movable so that the tape can be molded to form a smooth, plaster-like cast. When formulating the coated casting tapes of this embodiment one must strike a balance between the material's uncured "handling" properties (such as moldability, smoothability, resistance to pooling, etc.) and the material's cured physical properties (such as strength, surface smoothness, etc.). It is presently believed that the material's physical properties are substantially affected by the composite's filler to resin volume ratio. Unfortunately, as the filler to resin ratio is increased (thereby increasing the coating's viscosity and resistance to pooling) the composite may become less smoothable and more difficult to mold. In contrast, if the filler to resin ratio is too low, the coating may pool from the scrim backing or may not be able to be coated at a sufficiently high coating thickness or weight and thus not provide a cast having sufficient strength or rigidity.

A porous composite's handling properties may be characterized by measuring the resin component's viscoelasticity using a suitable rheometer. A suitable rheometer for evaluating the preferred materials of the present invention include cone and plate or parallel plate rheometers such as the Rheometrics Dynamic Analyzer-II ("RDA-II"), available from Rheometrics Inc. When operated in a dynamic shear mode the rheometer is capable of measuring the elastic- or storage- modulus (G'), viscous- or loss- modulus (G"), and dynamic viscosity ($\eta_o$) of the material. The ratio of G" to G' is referred to as tan delta (tan δ) and is a good measure of the material's overall viscoelastic behavior. In general, tan δ is greater than 1 for a liquid and less than 1 for a solid. When operated in a steady shear mode a parallel plate rheometer is capable of measuring the viscosity (η) as a function of the applied shear rate (γ).

As previously mentioned, dramatically decreasing the tan δ of the resin component is one method of enhancing the porous composite's (i.e., the resin and filler mixture's) cohesiveness and may be accomplished in a variety of ways. These include: (1) incorporating (i.e., solubilizing) a suitable amount of a high molecular weight secondary polymer into the curable resin; (2) forming an interpenetrating polymer network with the curable resin, e.g., by forming a secondary polymer in-situ through use of a co-cure polymer system; or (3) providing a high concentration of urethane, urea, or other hydrogen bonding functionalities to promote chain interaction; or (4) incorporating prepolymers with a relatively high level of chain branching thereby promoting chain entanglement. Combinations of the above methods may also be employed.

Suitable high molecular weight secondary polymers are those polymers which are sufficiently soluble, dispersible or swellable in the curable resin and are capable of decreasing the resin's tan δ. Suitable secondary polymers may actually bring the resin to a gel state. Particularly preferred polymers are those polymers which are capable of hydrogen bonding or otherwise interacting with the curable resin system in order to provide adequate viscoelasticity at relatively low addition levels. In general, the amount of secondary polymer added to the resin should provide a suitable tan δ value to the resin (and therefore the necessary cohesiveness to the composite) yet not adversely impact the strength and integrity of the cured system. The amount of secondary polymer required to accomplish this function will often depend on the molecular weight of the polymer and the viscosity of the unmodified curable resin or composite. In general, polymer properties (including rheological properties) are much more dependent on the larger sized molecules in a sample than on the smaller ones. Therefore, the weight-average molecular weight value of a polydisperse sample is a much better indicator of the properties to be expected in a polymer blend than the number average molecular weight and will be used herein unless otherwise noted. When cohesiveness is achieved by incorporation of a high molecular weight polymer, preferred mixtures of polymer and curable resin comprise up to 30% polymer, more preferably between 1 and 20% polymer and most preferably between 2 and 12% polymer. Presently preferred high molecular weight secondary polymers for use in the resin systems of the present invention have a weight average molecular weight ("$M_w$") between about 30,000 and 5,000,000. More preferably, the high molecular weight secondary polymers have a weight average molecular weight between 100,000 and 3,000,000. Most preferably, the high molecular weight secondary polymers have a weight average molecular weight between 250,000 and 2,000,000.

A preferred polymer is a polymer which is capable of significantly decreasing the tan δ of the resin when added to the resin at concentrations less than about 20% and preferably less than about 10% by weight such that tan δ of the resin and polymer mixture is less than 20 at 1.0 rad/sec, more preferably less than 10 at 1.0 rad/sec, and most preferably less than 5 at 1.0 rad/sec. In addition, a preferred polymer is a polymer which is capable of significantly increasing the storage modulus of the resin when added to the resin at concentrations less than about 20% and preferably less than about 10% by weight such that G' is at least 0.1 dyne/sq cm at 0.1 rad/sec and 1 dyne/cm at 1 rad/sec. Preferably the polymer is capable of increasing G' to values over 1 dyne/cm and 10 dyne/cm at frequencies of 0.1 and 1.0 rad/sec respectively.

Polyvinylpyrrolidone ("PVP") and copolymers of N-vinylpyrrolidone have been found to be particularly useful polymers for decreasing the tan δ of polyurethane prepolymer systems. PVP is generally soluble in many polyethylene glycols and polytetramethylene glycols and may be directly added as solids and vacuum dried in-situ while heating between about 100° C. and 150° C. Atlternatively, resins systems comprising PVP and polyol may be dried azeotropically using an appropriate solvent followed by solvent removal. Once dissolved in the polyol the resin and polymer solution is preferably formulated under process conditions which prevent the separation of the PVP from the solution. It has also been observed that undried PVP is a particularly useful polymer for decreasing the tan δ of polyurethane prepolymer systems. It is presently believed that the moisture added to the resin system (i.e., when using undried PVP having up to about 5 wt.% water) causes chain extension of the prepolymer with a resulting increase in hydrogen bonding of the urea groups so formed. Presently preferred polyurethane prepolymer resin systems comprise between 1 and 8% polyvinylpyrrolidone in the resin (based on the total resin weight and exclusive of any filler). Presently more preferred resin systems comprise between 2 and 6% by weight PVP in the resin. Presently preferred polyvinylpyrrolidone for use in the presently preferred resin systems of the present invention has a weight average molecular weight between about 30,000 and 3,000,000. More preferably, the PVP has a weight average molecular weight between 100,000 and 2,000,000. Most preferably, the PVP has a weight average molecular weight between 250,000 and 1,500,000.

Other suitable polymers for use in the preferred polyurethane prepolymer resin system include acrylate copolymers such as copolymers of isooctyl acrylate and N-vinylpyrrolidone ("NVP"), copolymers of C1–C14 acrylates and methacrylates (such as butyl acrylate, butyl methacrylate, isooctyl acrylate, isooctyl methacrylate, acrylic acid, methacrylic acid and copolymers of butyl acrylate and hydroxyethyl methacrylate), acrylamides, and methacrylamides. Other suitable polymers are those polymers formed from monomers such as N-vinyl pyrrolidone, vinyl acetate and its hydrolyzed polymeric derivatives, styrene, olefins, acrylonitrile and the like. It should be pointed out that such suitable monomers can also be ionic or may contain substituent groups (such as amino, mercapto, hydroxy, and carboxyl groups) which are reactive with the primary polymer system. High molecular weight polyalkylene oxides (preferably having a molecular weight greater than 20,000, more preferably having a molecular weight greater than 100,000) such as polyethylene oxide, polypropylene oxide, and polybutylene oxide as well as block and random copolymers of these may also be useful as the secondary polymer system. Preferred polymers and copolymers include those based on butyl acrylate, butyl methacrylate, isooctyl acrylate, isooctyl methacrylate, acrylic acid, hydroxyethyl methacrylate, acrylamide, N-vinylpyrrolidone, and polyethylene oxide. It is understood that these polymers may be polymerized in-situ within the primary resin system or a component of the primary resin, polymerized in a solvent and added to the finished primary resin system, polymerized in a component of the primary resin system such as the polyol or isocyanate, or added to a component of the primary resin system such as the polyol or isocyanate.

An alternative method of providing a highly viscoelastic resin (thereby facilitating the formation of a cohesive composite) is by forming an interpenetrating polymer network with the curable resin, e.g., by forming a secondary polymer in-situ through use of a co-cure polymer system. One method of accomplishing this goal is by incorporating a second reactive monomer or oligomer system, which is independently reactive, into the primary curable resin. Suitable second reactive monomers or oligomers are preferably independently reactive from the primary curable resin and are capable of forming, in-situ, a high molecular weight secondary polymer. This method offers the potential advantage of allowing processing of the composite material into its final form, or close to its final form, while it still has a relatively low viscosity. The second reactive monomer or oligomer may then be polymerized to form a secondary polymer thereby increasing the viscoelasticity of the resin blend. For example, an unsaturated second monomer or oligomer (such as a mono- or poly- functional acrylate, methacrylate, acrylamide, or methacrylamide) may be added to an isocyanate functional prepolymer resin system. The second monomer or oligomer may then be polymerized through the use of, for example, heat and/or actinic radiation (visible or ultraviolet light, electron-beam, etc.) to form a polymer therein. This polymerization step may be performed during the manufacturing process or by the user. More preferably the second reactive monomer or oligomer may also contain functional groups which will allow the second polymer to react With the primary cure system. For example, acrylate or methacrylate alcohols (such as hydroxyethylmethacrylate "HEMA") are capable of reacting via a free radical mechanism to form a linear polymeric polyol. This polymer is capable of reacting with an isocyanate resin system. Alternatively, an epoxy homopolymerization may be performed through the use of suitable catalysts yielding a polymer containing hydroxyl groups which are capable of further reacting with the isocyanate functional resin. In systems where the second reactive monomer or oligomer also contains functional groups which will allow the formed second polymer to react with the primary cure system, the ratio of NCO groups to OH groups preferably should be controlled so that sufficient residual reactive isocyanate functionality remains thereby ensuring a rapid and complete cure during application of the device. In addition, the extent of crosslinking of the second reactive monomer or oligomer should be controlled in order to avoid excessive brittleness of the cured composite which may lead to cast breakage by a patient.

A further alternative method of providing a highly viscoelastic resin (thereby facilitating the formation of a cohesive composite) is by providing a composition having a high concentration of urethane, urea, or other hydrogen bonding functionality. Suitable additives comprise groups which are capable of promoting hydrogen bonding or polymer chain interaction within the uncured resin system or both. Alternatively, the resin may comprise components with high amounts of chain branching or higher molecular weight oligomers which promote chain entanglements. If desired, both methods may be employed in combination. In the previously discussed isocyanate functional polyurethane prepolymer systems, the incorporation of higher levels of hydrogen bonding functionality may be accomplished by increasing the number of urethane groups per unit weight of resin and/or incorporating urea groups formed by the reaction of primary or secondary amine functional materials with the isocyanate groups of the resin. The number of urethane groups per unit weight of resin may also be increased through the addition of water to the resin (with a commensurate loss of carbon dioxide). In general, the relative number of urethane groups in the resin will increase as the ratio of isocyanate equivalents to alcohol equivalents (NCO/OH ratio) of a particular resin system is decreased. Furthermore, the relative number of urethane groups in the resin can be increased by using polyols of lower equivalent weights (higher OH numbers). Additional chain entanglement may also be provided by incorporation of higher molecular weight polyol components and/or by increasing chain branching through the incorporation of polyols and/or isocyanates having a functionality greater than 2. The average functionality can be as high as 6 but is preferably less than 4 and is typically between 2 and 3. Where modification to the functionality of the resin is the primary means of increasing the viscoelasticity of the resin the functionality is preferably between 2.5 and 3.5. A sufficient amount of hard segment (e.g. isocyanate) should be provided to ensure adequate, stiffness for rigid immobilization applications. For systems based on Isonate 2143L the concentration of Isonate should be preferably greater than 45% by weight and more preferably greater that 50% by weight and most preferably greater than 54% by weight of the resin component (without filler) to ensure the final composite is sufficiently stiff.

As previously mentioned, the process of applying (e.g., wrapping) a cast to a patient's limb imparts a tensile force or stress to the casting bandage or tape. Similarly, the application of a splint to a patient's limb also stresses the splint material. Suitable casting or splint materials should readily accommodate these application stresses and not break apart during the cast application procedure. Preferred casting tapes of the present invention have a tensile strength greater than about 0.0175 N/mm width, more preferred casting tapes have a tensile strength greater than about 0.0875 N/mm width, and most preferred casting tapes have a tensile strength greater than about 0.175 N/mm width.

Traditional casting products distribute these stresses on a heavy-weight fabric backing or scrim (e.g., a fiberglass knit). In contrast, the present invention provides casting materials which in some cases have sufficient cohesiveness to resist these application stresses even without a heavy weight fabric backing or scrim (e.g., by decreasing the resin component's tan δ through the incorporation of a high molecular weight secondary polymer into the resin, etc.). However, a second alternative approach to increase the cohesiveness of the materials of the present invention, i.e. to impart higher tensile strength prior to curing and/or increased resistance to cracking during application and curing, is the incorporation of macrofibers into the composite (either as individual fibers or as a fabric scrim). In this approach, macrofibers provide enhanced cohesiveness to the composite and support some of the tensile forces which are placed on the uncured composite during application. This is particularly preferred for ease of processing the material. Most preferably, a light scrim may be utilized to perform this function. A combination of these approaches is also possible.

Suitable macrofibers for increasing the cohesiveness of the uncured composite include both inorganic fibers and organic fibers. Suitable inorganic fibers include: fiberglass, and ceramic fibers. Suitable organic fibers include fibers made from: polyester, polyamide (including nylon and Kevlar), polyolefin, polyacrylate, rayon, cotton, hemp, jute, natural rubber, and polyurethane materials. Blends of fibers may also be useful. Suitable fibers have average lengths at least 0.5 cm. Preferred fibers have average lengths between 0.5 and 8 cm, more preferably the fibers are between 1 and 5 cm in length. The fibers may be multifilament or monofilament materials and may comprise filaments between 0.5 and 300 denier. It has been found that incorporation of as little as 1 to 2% by weight of polyester fibers results in a significant improvement in web integrity and cohesiveness. It is presently believed that incorporation of from 1 to 30% by weight of a suitable fiber may be beneficial.

As previously mentioned, it may be beneficial to incorporate a light conformable scrim into the material. This approach is presently preferred when fabricating orthopedic casting tapes which are highly smoothable and moldable. One such presently preferred tape is described in further detail in Example 24. The scrim may be on the surface of the composite but is preferably embedded or partially embedded in the material. Preferred scrims are light-weight and generally comprise less than 30%, more preferably less than 20% by weight of the composition. The light-weight nature of these preferred scrims does not permit complete absorption of the binder into the fiber bundles. Consequently, a significant amount of composite mixture (e.g., resin and filler) lies atop the scrim and is "available" for molding and conforming. The available composite mixture can in some instances move relative to the light-weight scrim and form a very smooth cast surface. Notably, preferred composite mixtures for use with preferred light-weight scrims have sufficient viscosity or yield stress to resist undesirable "pooling" during normal use and storage. Preferred composite mixtures have a viscosity of at least 100 Pa s, more preferably at least 400 Pa s, most preferably at least 1,000 Pa s when tested at 1 rad/s.

The scrims are preferably porous to allow the composite coated scrim to pass moisture, vapor, and air. Preferred scrims are thin with fairly large openings in order to allow bonding of the material on either side of the embedded scrim. Suitable scrims include knits, wovens, non-wovens and extruded porous sheets (e.g. materials from Conweb, Minneapolis, Minn.). Cheese cloth has proven to be quite useful. Preferred scrims have a basis weight between 5 and 30 grams/m$^2$, more preferably between 8 and 26 grams/m$^2$, most preferably between 8 and 17 grams/m$^2$. A light-weight scrim (6 grams/m$^2$) comprising 1.75 denier, 3.8 cm long polyester staple fibers and coated at a basis weight of 2 grams/m$^2$ with Roplex B15 resin (available from Rohm & Hass Co., Philadelphia, Pa. 19105) is particularly suitable. Another suitable light-weight and low cost scrim is a spun-bonded nonwoven made from polymers including polypropylene, polyester, polyethylene, and polyamide. Because of its low cost and drapability polypropylene is the preferred polymer. A suitable spunbonded polypropylene nonwoven with good openness to allow sufficient water penetration through a roll of coated nonwoven during water activation and sufficient conformability when wrapping the material is RFX™ nonwoven fabric (available from AMOCO Fabrics and Fibers Company, Atlanta, Ga.) in a basis weight of 16.7 g/m$^2$. Other webs may be substituted if desired.

If desired, a heavier scrim such as a traditional fiberglass knit may be utilized in the casting products of the present invention. While this is not preferred, for the reasons previously mentioned, fiberglass knits provide sufficient support and porosity. Suitable scrims for use in the present invention are disclosed in pending U.S. patent application Ser. No. 08/008,751, which is herein incorporated by reference. Where fiberglass backings are desired, suitable sheets which may be employed are knit fiberglass fabrics such as disclosed in U.S. Pat. Nos. 4,502,479; 4,609,578; 4,668,563; and 5,014,403 and in U.S. patent application Ser. No. 07/976,402, now U.S. Pat. No. 5,353,486. Particularly preferred sheets of this type are extensible, heat-set fabrics as disclosed in U.S. patent No. 4,609,578 (Reed) which is herein incorporated by reference. When heavier-weight scrims are employed, suitably heavier coating weights may also be employed to maintain a smoothable feel to the sheet. Preferably, the coating weight of composite mixture (e.g., resin and filler) is greater than the weight which is absorbed by the fiber bundles of the sheet. This ensures that a portion of the composite mixture is available at the surface of the sheet to provide the preferred smoothable feel.

In practice the scrim may be incorporated between two thin sheets of highly filled resin composition. Alternatively, more than one scrim may be utilized to form a laminate sheet with the highly filled resin composition. For example, two scrims may be used to "sandwich" a sheet of highly filled resin composition. This can be accomplished by pressing the scrims against the surfaces of a sheet of highly filled resin composition, e.g., through a nip roller. In addition, the scrim may be pre-coated with a resin which facilitates bonding of the adjacent layers of highly filled resin composition. The pre-coated resin may be similar to the resin in the composite or may comprise a different composition, such as a pressure sensitive adhesive.

A preferred process for making a casting tape comprising a coating of a highly filled composite mixture (comprising curable resin and filler) on a light-weight scrim involves coating the composite mixture on the scrim while the composite mixture viscosity is relatively low. In one presently preferred method the composite mixture is coated on the light-weight scrim while the curable resin is only partially reacted (i.e., the curable resin at the time of coating comprises a mixture of prepolymers). Thus, the coating has a low enough viscosity to spread out on the scrim. Additional filler may then be dusted on the surfaces of the coated scrim if desired. This process is further described in Example 24. In another method the composite mixture may be diluted with a volatile solvent which lowers the viscosity of the mixture and which is readily removed after being coated on the scrim.

The present invention also provides casting materials containing resins which possess a smoothable feel during application. It has been found that the initial water absorbency of a resin system can be controlled by the proper selection of polyol and isocyanate and, if present, the secondary polymer. For example, these components can be blended to provide a resin which is sufficiently hydrophilic to allow the resin to become smoothable and feel "movable" or actually allow movement of the resin much like plaster of Paris. This facilitates a smooth finish to the cast and greatly enhances cast moldability.

Incorporation of suitable amounts of a hydrophilic polyol such as polyethylene glycol into the resin formulation provides a smoothable resin upon water activation. Yet even when the resin becomes movable no mess is created if the filler level of the composite is maintained high enough and/or the resin is sufficiently viscoelastic. Nevertheless, as the resin becomes even more movable it may be necessary for the clinician to wear gloves to avoid transfer to the hands. Preferred composite systems incorporate a sufficient amount of hydrophilic components to provide a movable resin. For systems that comprise a polyisocyanate prepolymer resin, creamy movable composites can be prepared by increasing the curable resin's NCO/OH ratio which generally results in more free isocyanate and in a decreased resin viscosity. Suitable smoothable resins have an NCO/OH ratio greater than 2.0. Preferred smoothable resins have an NCO/OH ratio greater than 2.5, more preferably greater than 3.0, most preferably between 3.0 and 3.9. As used herein "movable" or "movable resin" refers to a resin which after activation with water but before setting becomes smoothable on the surface and can be physically redistributed by hand to smooth the surface of the molded cast in a manner similar to a plaster of Paris cast although perhaps not to the extent possible with plaster of Paris. As a result, the moldable materials of the present invention do not appreciably stick to the gloves of the applier, nor drip significant amounts of material onto the floor causing a mess.

Smoothability of the composite is important because it allows the use of inexpensive fabrics which may not conform perfectly to the shape of the body part simply by wrapping the material on. The smoothability of the composite allows any tucks and folds to be blended into the cast. In addition, smoothability allows the practitioner to make a smooth cast which is non-abrasive to the patient's skin and clothing. Furthermore, smoothability greatly increases the ease of molding the cast for the desired fit and clinical requirements for proper healing. Smoothability in the present invention is defined as the ability to sufficiently smooth the curable or hardenable portion of the casting tape or splint by hand rubbing to produce an even surface. Preferably, the texture of the scrim, and any overlap areas resulting from wrapping and folding of the tape become blended into the surface so as to make these features no longer readily apparent.

To achieve the smoothability of the present invention, the composite must have a sufficiently low viscosity when water activated. This can be controlled by adjusting the resin composition and filler content as described previously. For example, higher NCO:OH ratios and lower filler levels reduce the viscosity. When measured according to Example 30, the viscosity of the water activated material is preferably less than $2.5 \times 10^4$ Pa s, more preferably less than $1.8 \times 10^4$ Pa s, and most preferably less than $1.2 \times 10^4$ Pa s. In addition, the composite preferably contains a slip agent or lubricant to prevent the composite from sticking to the gloves of the applier and thus allow easy movement of the hands over the surface of the cast being formed. Suitable lubricants are described in U.S. Pat. No. 4,667,661. Furthermore, the composite must be available in sufficient quantity on the surface of the scrim to allow for the desired smoothability. Traditional synthetic casting materials contain the resin within the fiber bundles of the fabric, thereby making the resin unavailable for smoothing the surface of the cast made therefrom. To make sufficient composite available for smoothing purposes it is desired that at least a 50 micron thickness of composite be available on the exposed surfaces of the fibers comprising the scrim upon which the composite is coated. More preferably, at least a 100 micron thickness of composite is available, and most preferably a 150 to 300 micron thickness of composite is available.

Resin systems may also be colored for decorative purposes using dyes or pigments or both. Luminescent pigments may also be employed. Furthermore, one may alternatively wrap the splint or cast of the present invention with a decorative or informative sheet comprising raised lettering and/or figures which is capable of leaving impressions in the material. Furthermore, the materials of the present invention may be printed using suitable dyes or pigments by direct or indirect printing methods such as transfer printing, pigment printing, or ink jet printing.

Figure 6:
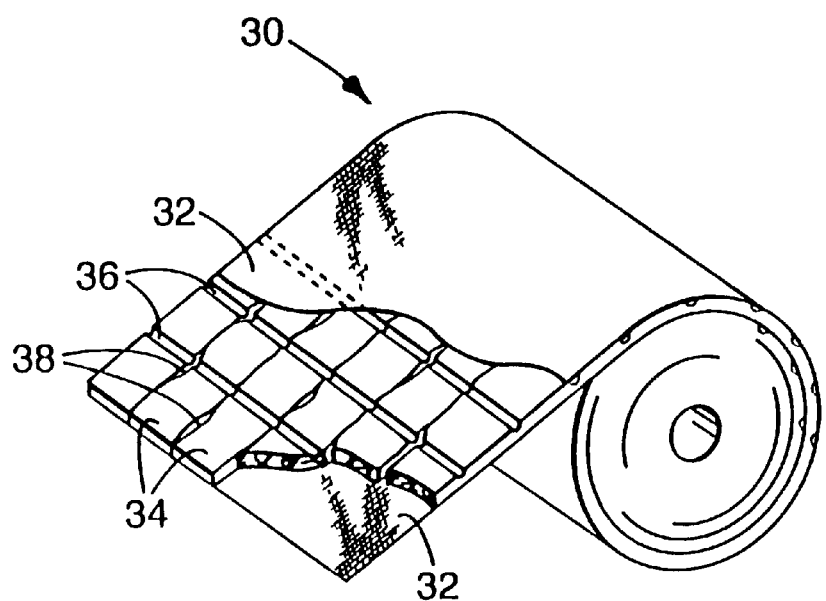
FIG. 6 shows a breakaway perspective view of a roll form casting tape comprising a composite casting material, formed from a plurality of narrower strips of casting material, sandwiched between two layers of a light-weight scrim material.
Figure 7A:
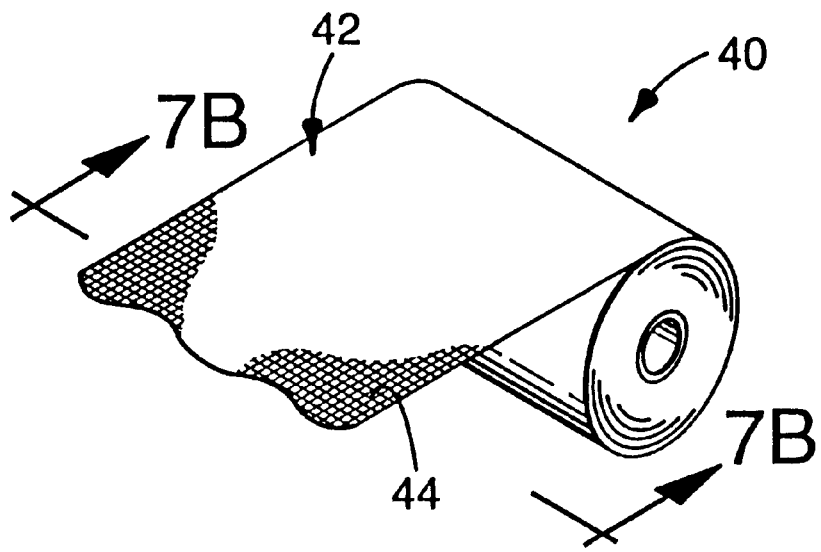
FIG. 7a shows a perspective view of a casting tape comprising a mixture of a curable resin and filler coated on a light-weight scrim.
Figure 7B:
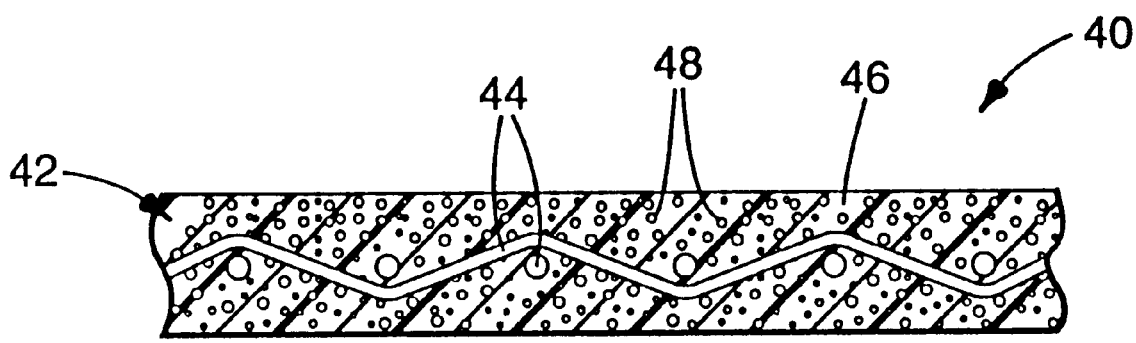
FIG. 7b shows a cross-section view of the casting tape of FIG. 7a along lines B—B.
Figure 8:
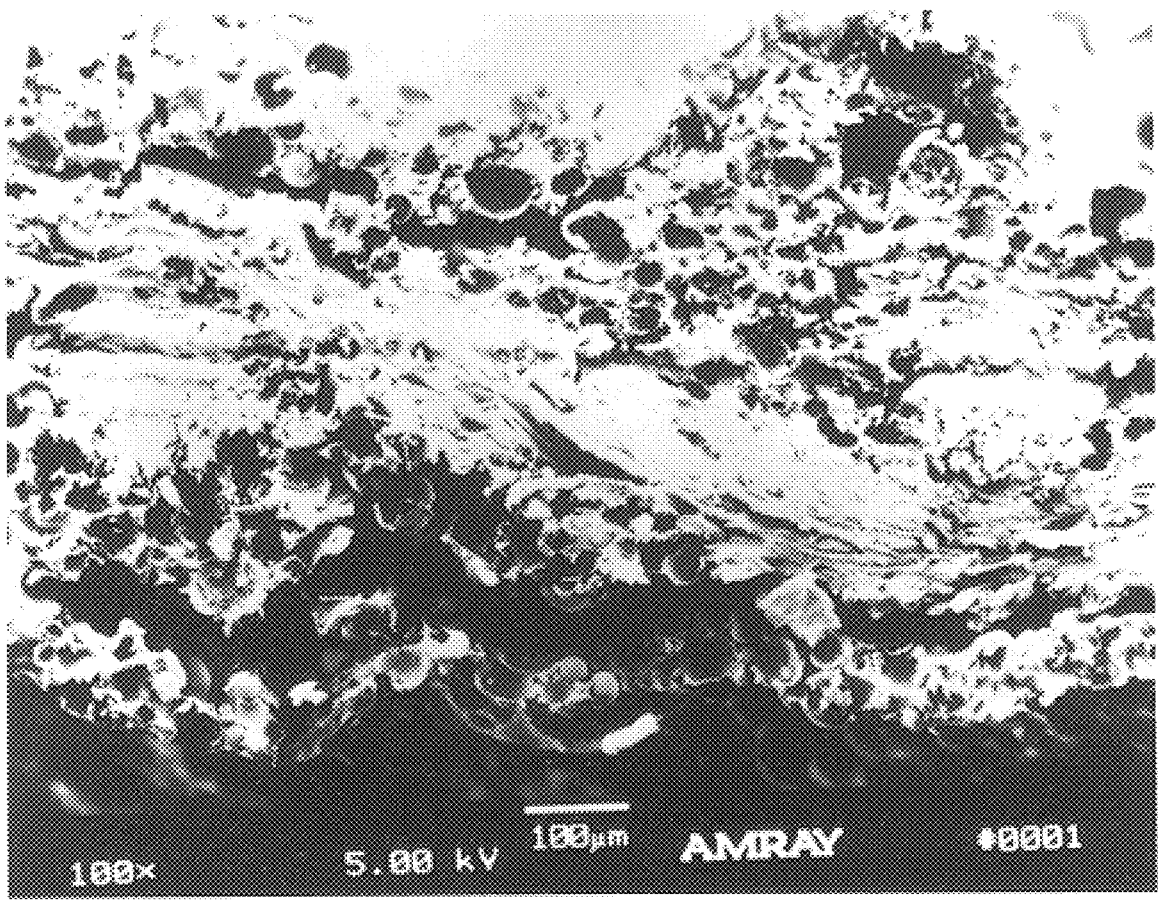
FIG. 8 is a scanning electron micrograph of the cross-section of the casting material of Example 31.

The materials and compositions of the present invention may be fabricated into a variety of configurations including splints, tapes, and preformed shapes such as tubes. When fabricated as a splint, the material may be provided as a precut slab or a continuous length form with or without a covering and/or padding. Suitable coverings and paddings for use in this invention are discussed in U.S. Pat. Nos. 5,027,803 and 4,899,738 which are herein incorporated by reference. The splint may have a padding material on one or both sides. The materials and compositions of the present invention may also be supplied as a prepadded unitary splint in tubular form such as that illustrated in FIG. 6 of U.S. Pat. No. 5,027,803.

A fugitive water soluble web may be employed as a liner which separates adjacent layers of the tape (e.g., when the tape is provided as a roll) and which may enhance the tape's cohesiveness. When used with a water curable resin the liner is preferably dried prior to being placed in contact with the resin. Preferably, the liner is rapidly soluble in water and effectively dissolves when exposed to water in less than about 60 seconds (as defined in the examples below), more preferably the liner dissolves when exposed to water in less than 30 seconds and most preferably the liner dissolves when exposed to water in less than 10 seconds. Preferred liners also provide a lubricating effect to the tape when dissolved. By "effectively dissolve" is meant that the liner when mixed with water under the desired conditions of use will solubilize in the water to an extent sufficient to provide a lubricating effect or allow layer-to-layer adhesion of the casting material or both. More preferably the liner when mixed with water under the desired conditions of use dissolves to form a homogeneous liquid mixture. Suitable water soluble liners are comprised of polymers such as polyvinylalcohol ("PVA") and copolymers of PVA (as used herein, the term polyvinylalcohol refers to copolymers derived from, for example, the hydrolysis of polyvinyl acetate, wherein the extent of hydrolysis is preferably greater than 50 percent, more preferably greater than 80 percent), polyacrylamides, polymers incorporating acrylic acid, cellulose ether polymers such as hydroxypropylmethylcellulose, hydroxypropyl cellulose, and hydroxyethylcellulose, polyethyloxazoline, polyethylene oxide (as used herein "polyethylene oxide" and "polyethylene glycol" are synonymous terms), polyethylene oxide and polypropylene oxide random and block-copolymers, esters and urethanes of polyethylene glycol or polyethylene glycol and polypropylene glycol polymers and the like. Copolymer films and laminates and polymer blends are also possible.

Preferably the liner has sufficient flexibility for processing. Some liner materials (e.g., certain PVAs) may require the incorporation of a plasticizer to achieve a suitable degree of flexibility for use as a liner. Suitable plasticizers may be incorporated into the liner either "internally" or "externally" to the polymer component. An example of a plasticizer which is "internally" incorporated into the liner is a polymer formed by copolymerizing vinyl acetate with polyethylene glycol monomethacrylate (the plasticizer) followed by hydrolysis to PVA and extrusion as a film. An example of a plasticizer which is "externally" incorporated into the liner is the blending of glycols or other small molecules such as esters into a polymer melt. The plasticizer preferably is extremely dry for use with the presently preferred water curable resins. However, for thermoplastic casting materials a low concentration of water may serve as the plasticizer. Suitable liner films include continuous or non-continuous films. Suitable non-continuous films include continuous or non-continuous such as melt blown PVA films. Being in a non-continuous form such as a non-woven fabric may facilitate dissolution of the liner due to the greatly exposed surface area. Furthermore, porous structures may also provide greater flexibility which may facilitate processing. In use the liner begins dissolving as soon as the product is contacted with water and therefore need not be removed or even perceptible to the clinician. Liners are preferably kept thin to prevent excessive build up of polymer solution which could interfere with layer to layer lamination of the casting tape. Continuous film liners are preferably less than 100 $\mu$m thick, more preferably less than 60 $\mu$m thick, and most preferably less than 25 $\mu$m thick. While the liner itself provides lubrication, an additional lubricant such as disclosed in U.S. Pat. No. 4,667,661 may be added to the composition.

The presently most preferred liner for use with water-curable casting tapes is Aicello Solublon PVA film SA grade 17 micron thick available from Mitsui Plastics Inc. (White Plains, N.Y.). Although, even when dry, this film is potentially reactive with isocyanate functional water-curable resins (since it contains "hydroxyl" functionality) it has been observed that this reaction does not readily occur. It is presently believed that undesirable reactions between such liners and resins can be prevented provided the liner and resin are maintained in a separate "phase"(i.e., the liner should preferably be essentially insoluble in the resin).

For purposes of retarding resin migration (e.g., on systems where the resin is susceptible to "pooling") the liner is preferably a continuous film and is wound up along with the casting tape such that through the cross section of the roll the layers of casting tape and liner alternate. Alternatively, the liner may be placed on both sides of the casting tape during the winding operation. Furthermore, the liner, if placed on both sides of the casting tape, may be sealed on one or both edges to further prevent resin pooling and migration. In the absence of such a seal, and in order to gain the full benefit of this embodiment, the roll of casting tape is preferably stored laying on its side rather than on an end. If stored on an end, with an unsealed edge downward, the resin could possibly still pool. However, since many casting tapes are currently boxed and stored on their sides this may not be a problem.

In another embodiment of the present invention a thermoplastic polymer is employed as a binder (i.e., a casting tape or splint is provided as a "thermoplastic" composite). This embodiment offers an environmentally friendly and hazard-free alternative in casting. Casting materials of this embodiment do not require cumbersome disposable liners and will provide a moldable slippery material which is easy to apply. In addition, the product will have very good conformability and should be inexpensive to manufacture.

The basic elements of the thermoplastic composite of the present invention include: a thermoplastic polymer with controlled amorphous phase rheology, the thermoplastic polymer preferably being softened at less than about 75° C.; an optional water soluble liner; and a substantial proportion of inert fillers as previously described. The thermoplastic casting tapes of the present invention may also comprise components containing one or more reactive functional groups suitable for cross-linking the article.

Suitable thermoplastic polymers for use in the present invention are those polymers which soften or melt at temperatures which can comfortably be withstood by the patient and/or technician during the cast's application. This temperature is believed to be less than about 90° C., preferably less than about 75° C., although somewhat higher temperatures may be acceptable (especially in situations where direct contact of the casting material and skin are avoided). Suitable thermoplastic polymers include polyurethanes (especially polyurethanes based on semi-crystalline polyester polyols), polyethylene, ethylene vinyl acetate, cis and trans polyisoprene, polyesters such as polycaprolactone and the like. The currently preferred thermoplastic polymers for use in the present invention are semi-crystalline polyesters. Polycaprolactone and blends of polycaprolactone are particularly preferred.

In this embodiment the thermoplastic polymer is substituted for the curable resin and provides a similar function (i.e., holding the filler together). Thermoplastic casting materials are applied to the patient after first heating the material above its softening temperature (e.g., in the case of semi-crystalline materials above their melt temperature). Heating of the material may be accomplished in a variety of ways including immersion in hot water, contact with steam, exposure to microwave radiation, contact with dry heat, etc. The use of water or steam is particularly preferred in product constructions which incorporate a water soluble liner and/or hydrophilic resin lubricant. Microwave heating is suitable for materials which absorb microwave energy or employ a microwave susceptor. The warmed casting material is then molded to the desired shape and cooled to harden.

The following examples are offered to aid in understanding of the present invention and are not to be construed as limiting the scope thereof. Unless otherwise indicated, all parts and percentages are by weight.

EXAMPLES

Example 1

Casting Article Comprising Resin and Glass Bubbles

To a beaker containing 13.3 g of glass bubbles (having a specific gravity of 0.60 and available as "SSX" from 3M Company, St. Paul, Minn.) was added 26.6 g of a resin consisting of components shown in the following table:

TABLE 1

| Component | Parts |
| --- | --- |
| Isonate 2143L (Dow Chemical Co.) | 54.83 |
| MEMPE[1] | 1.75 |
| Benzoyl chloride | 0.07 |
| DB-100 Silicone Fluid[2] | 0.18 |
| IONOL[3] | 0.49 |
| Arcol PPG 725 (Arco) | 42.68 |

[1]"MEMPE" = 4-[2-[1-methyl-2-(4-morpholinyl)ethoxy]ethyl]morpholine.
[2]Now known as Dow Corning Antifoam 1400.
[3]"IONOL" = 2,6-di(tertiarybutyl)-4-methylphenol or "BHT".

In a dry environment (i.e., less than 4% relative humidity) the mixture was stirred with a spatula, then kneaded. An additional portion (3 g) of glass bubbles was added and kneaded in to provide a dry to the touch putty-like composite which was 38% by weight filler and had a ratio of filler volume to resin volume ($V_f/V_r$) of 1.06.

Curing of the composite was initiated by placing it under running tap water having a temperature of approximately 25° C. The moist composite was molded around two fingers and cured in 2 to 4 minutes. The composite was easy to mold and very conformable during curing. It was smooth and snow white. After curing for 24 hours it was strong enough to permit a person weighing 63.5 kg to stand upon the composite on the fingers without damaging the composite.

Example 2

Casting Article Comprising Resin, Glass Bubbles and Cheesecloth

A 300 g portion of poly(N-vinyl)pyrrolidone (having a weight average molecular weight of 360,000 and available from Aldrich Chemical Company, Milwaukee, Wis.) was added to a 5 liter flask containing 2700 g of Carbowax 600 polyol preheated to 49° C. (available from Union Carbide, Danbury, Conn.). The aforementioned polymer is hereinafter referred to as "PVP-360." A vacuum (0.5 torr) was drawn upon the closed flask and the mixture was slowly heated to 120° C. and maintained at that temperature for a total of 2 hours until water evaporation stopped in order to dry the mixture. The solution obtained was cooled to about 49° C. and stored in a 49° C. oven.

Resin was formulated by mixing the ingredients shown in the following table in the order shown. The mixture was warmed and shaken vigorously by hand for 5 to minutes after the addition of the Carbowax 600/PVP-360 solution until a homogeneous solution resulted. After all components were added the mixture was placed on a shaker for 0.75 hour, then allowed to stand for about 16 hours at 25° C.

TABLE 2

| Component | Parts |
| --- | --- |
| Isonate 2143L | 384.82 |
| Carbowax 600/PVP solution | 215.30 |
| Benzoyl Chloride | 0.35 |
| DB-100 | 1.26 |
| Ionol | 3.36 |
| MEMPE | 10.50 |
| Carbowax 1450 polyol | 112.39 |

In a first batch, to 40 g of Scotchlite™ H50/10,000 EPX glass bubbles (having specific gravity of 0.5 and available from 3M Company) which had been dried by eating at 140° C. for about 16 hours was added 26.7 g of the resin from Table 2. The mixture was kneaded by hand until it was homogeneous, then rolled flat into a 9.53×0.5×0.635 cm teflon mold lined with PVA film (Aicello Solublon SA grade, Mitsui Plastics Inc., White Plains, N.Y.) using a teflon coated metal rolling pin. The composite was removed from the mold and the PVA film was peeled off. The resulting composite ($V_f/V_r=3.1$) was placed flat and stored in a conventional cast pouch of polyethylene coated aluminum foil.

In a second batch, to 40 g of Scotchlite™ H50/10,000 EPX glass bubbles which had been dried by heating at 140° C. for about 16 hours was added 26.7 g of the resin from Table 2 resulting in composite having $V_f/V_r=3.1$. The batch was separated into two approximately equal portions, one of which was formed into a composite layer 3.18 mm thick in the previously described teflon mold. A layer of conventional commercially available cheese cloth which had been impregnated with a small amount of the resin of Example 1 was placed over the composite layer and the second half of the batch which shad also been formed into a 3.18 mm layer in the same teflon mold was sandwiched over the cheese cloth. The laminate was rolled with the teflon coated metal roller pin to ensure the layers were well bonded and stored in a polyethylene-coated aluminum foil pouch.

A third casting article was prepared by adding 28.5 g of Dicaperl HP 900 glass bubbles (having a specific gravity of 0.33 and available from Grefco Inc., Torrence, Calif.) to 27 g of the resin of Table 2 and kneading until the mixture (having a $V_f/V_r=3.32$) was homogeneous, then separating the batch into two equal portions, forming a laminate of 3.18 mm thickness as described above around untreated cheesecloth and rolling the laminate with a roller pin. While the laminate did not separate, it is believed that they would separate more easily than the laminate described as the second batch. It was stored in a standard polyethylene-coated aluminum foil pouch.

Each of the laminated casting articles of the present Example was removed from the storage pouches and immersed in warm water to initiate curing. Casts were formed on the arms of volunteers over conventional stockinette, then the casts were wrapped with 7.62 cm Coban® elastomeric bandage (available from 3M Company, St. Paul, Minn.) and manipulated to conform to the arms. The casting articles had set after several minutes and were allowed to cure over several hours to form strong, durable casting articles. The laminated articles cured rapidly and were very conformable. The cured article's hardened surface reproduced the surface pattern of the elastomeric bandage, indicating the exceptional moldability of the material.

Example 3

Casts Comprising Viscoelastic Resin and Glass Bubbles

A resin was formulated by mixing the ingredients shown in the following table as described below.

TABLE 3

| Component | Equiv. wt. | Parts | Weight (g) |
| --- | --- | --- | --- |
| Isonate 2143L | 144.4 | 55.66 | 222.65 |
| MEMPE | 129.5 | 1.53 | 6.13 |
| Terathane 1000 | 490 | 35.46 | 141.83 |

TABLE 3-continued

| Component | Equiv. wt. | Parts | Weight (g) |
| --- | --- | --- | --- |
| Arcol LG-650 | 86.9 | 3.35 | 13.38 |
| PVP-360 | | 4.0 | 16.00 |

Solid PVP-360 was added to Terathane 1000 polyol (available from Dupont, Wilmington, Del.) in a ratio of 1 part PVP-360 to 9 parts Terathane in a stirred 5000 ml flask. The mixture was heated to 120° C. under a vacuum of 0.7 torr to provide a clear viscous material. The vacuum was held until the solution was dry and no further bubbling was evident. A portion (157.83 g) of this material was added to a homogeneous mixture of 13.38 g of LG-650 in 222.65 g of Isonate 2143L and the mixture was stirred and warmed until a clear homogeneous solution resulted. The MEMPE was added and the mixture was placed on a shaker for one hour in a sealed insulated jar. On cooling the resin was elastic, showing a significant rebound force, and capable of forming a film when placed between two gloved hands and the hands slowly separated.

A casting article was prepared in a dry environment (i.e., having less than 4% relative humidity) by adding 60 g of Scotchlite™ H50/10,000 EPX glass bubbles (available from 3M Company, St. Paul, Minn.) to 40 g of the above resin. The mixture ($V_f/V_r=3.12$) was stirred, then kneaded by hand to provide a homogeneous conformable mixture. The mixture was spread and formed in a 9.53×30.5×0.635 cm teflon mold lined with a PVA film as described in Example 2 using a teflon coated rolling pin. The article was removed from the mold, the PVA liner was peeled off and discarded. The article was placed flat and stored in an airtight polyethylene coated aluminum foil pouch.

To determine the usefulness of the article it was removed from the pouch (gloves were not needed) and immersed in a stream of warm tap water for several seconds. It was then applied to an arm covered with conventional casting stockinette. The article was next overwrapped with a 7.62 cm wide Ace-type elastic bandage and molded to conform to the arm. The casting article had set in less than 5 minutes. When the Ace bandage was removed to examine the article it was found that excellent conformance to the arm was obtained. Notably, even the texture of the stockinette was apparent in the cured molded article. After 24 hours the cured article was sufficiently strong and weight bearing that an adult weighing 63 kg could stand on it without breaking it.

Example 4

Casting Artide Comprising Glass Bubbles and Various Elastic Resins

The following resins were formulated to evaluate their potential for use with glass bubble fillers.

TABLE 4a

| Component | Equiv. wt. | Parts | Weight (g) |
| --- | --- | --- | --- |
| Isonate 2143L | 144.4 | 52.4 | 228.45 |
| Benzoyl Chloride | | 0.05 | 0.21 |
| Antifoam 1400 | | 0.17 | 0.74 |
| Ionol | | 0.45 | 1.98 |
| MEMPE | | 1.09 | 4.74 |
| Pluronic F-108[1] | 7250 | 3.78 | 16.50 |
| PPG-425 | 212.50 | 9.88 | 43.08 |

TABLE 4a-continued

| Component | Equiv. wt. | Parts | Weight (g) |
|---|---|---|---|
| PPG-725 | 378.3 | 26.78 | 116.76 |
| Secondary Polymer[2] | | 5.4 | 23.54 |

[1]Available from BASF Wyandotte Corp., Parsippany, NJ.
[2]As described below in Table 4b.

TABLE 4b

| Polymer # | Secondary polymer employed[1] | $M_w$ | $M_n$ |
|---|---|---|---|
| 1 | IOA[2]/acrylamide (96/4) | 2,143,100 | 178,982 |
| 2 | IOA/acrylamide (93/7) | 1,718,272 | 217,321 |
| 3 | IOA/NVP (91/9) | 1,940,328 | 183,965 |
| 4 | HEMA[3]/butyl methacrylate (30/70) | — | — |

[1]Described as a ratio by weight of comonomers.
[2]"IOA" = Isooctyl acrylate.
[3]"HEMA" = Hydroxyethyl methacrylate.

In order to prepare the resins a solution of the secondary polymer in PPG 725 polyol was first prepared (i.e., the polymers of runs 1, 2, and 3 comprising 18–24%; 22–27% and 25–28% solids respectively in a heptane and ethyl acetate solvent mixture were dissolved in the PPG 725). The solvents were then removed by evaporation in vacuo.

Polymer 1 was not soluble in PPG 725, polymer 2 was soluble but precipitated when resin formulation was attempted, and polymer 3 gave an excellent elastic resin. Polymer 4 was dissolved and dried in Terathane 1000 at 10% by weight by heating under vacuum (0.5 torr) at 100° C. to give a clear solution which was a good candidate for resin formulation in a resin such as that shown in Table 3 of Example 3.

Example 5

Resins for Use With Glass Bubble Fillers

The following resins were formulated to evaluate their potential for use with glass bubbles. Each mixture was made in an 227 ml jar and mixed on a roller for about 16 hours.

TABLE 5

| Component | Resin 5-1 | Resin 5-2 | Resin 5-3 |
|---|---|---|---|
| Isonate 2143L | 125.89 g | 113.21 g | 99.89 g |
| MEMPE | 0.0 g | 3.5 g | 3.5 g |
| PPG-425 | 74.11 g | 83.3 g | 97.31 g |
| NCO/OH ratio | 2.5 | 2.0 | 1.5 |

Resin 5-1 was acceptable with moderate viscosity. Resin 5-2 appeared to be very viscous and perhaps elastic but very stiff. Resin 5-3 was too hard and stiff to be manipulated by hand.

Example 6

Casting Article Comprising Resin, Glass Bubbles and Polymer Fibers

A casting article was prepared by combining 19.9 parts of the resin of Example 2 with 19.9 parts of the resin of Table 6 and adding 58.8 parts glass bubbles (Scotchlite™ H50/10,000 EPX, available from 3M Co., St. Paul, Minn.) and 2 parts of 1.5 denier 1.9 cm polyethylene terephthalate fibers (available from Minifibers Co., Johnson City, Tenn.).

TABLE 6

| Component | Equiv. wt. | Parts |
|---|---|---|
| Isonate 2143L | 144.4 | 55.66 |
| MEMPE catalyst | 129.5 | 1.53 |
| Terathane 1000 | 490 | 35.46 |
| Arcol LG-650 | 86.9 | 3.35 |
| PVP-360[1] | | 4.0 |

[1]Predissolved in the Terathane 1000

The resins were mixed with Scotchlite™ H50/10,000 EPX glass bubbles and 1.5 denier filaments of 1.9 cm length polyethylene terephthalate, spreading the filaments by mixing well. An article was molded in a teflon mold as described in Example 2 first batch except without a PVA liner. The resulting composite was placed flat and stored in a conventional cast pouch of polyethylene coated aluminum foil.

The casting article of the present Example was removed from the storage pouch. Curing was initiated with warm water and a cast was formed on the arm of a volunteer over conventional stockinette, then the cast was wrapped with a 7.62 cm Coban® elastomeric bandage and manipulated to conform to the arm. The casting article had set after several minutes and was allowed to cure over several hours to form a strong, durable casting article. The article cured rapidly and was very conformable.

Example 7

Casting Article Composites

Several casting materials were formulated using varying amounts of two casting resins and percent catalyst. Glass bubbles were added to each resin to provide casting composite articles for property evaluation. The resins were formulated using the ingredients listed in Tables 7a and 7b.

TABLE 7a

| Ingredient | Resin A (g) | Resin B (g) |
|---|---|---|
| Benzoyl chloride | 0.13 | 0 |
| Isonate 2143L | 384.82 | 389.4 |
| MEMPE catalyst | 3.14 | amount varied |
| DB-100 | 0.47 | 1.26 |
| Ionol | 1.26 | 3.36 |
| Carbowax 606 polyol | 187.31 | 0 |
| Carbowax 1450 polyol | 112.41 | 0 |
| PVP-360 | 10.46[1] | 28.0[2] |
| Terathane 1000 polyol | 0 | 285.8 |
| Mesitylene sulfonyl chloride | 0 | 0.56 |

[1]Dissolved and dried in the Carbowax 600
[2]Dissolved and dried in the Terathane 1000

Resin A was prepared in a glass vessel under a stream of nitrogen gas. A arm (about 49° C.) mixture of polyol and PVP was mixed with the Isonate and the mixure was shaken until uniform dispersion occurred. The other ingredients were added (catalyst last) then the mixture was shaken again.

Resin B was prepared by adding the warm (49° C.) polyol/PVP-360 mixture to the Isonate, mixing, then adding the other ingredients in the order: Ionol, DB-100 and Mesitylene Sulfonyl Chloride. The resins were mixed according to the proportions listed in Table 7b. The catalyst was added last.

The articles were made by hand mixing 40 g of resin (or resins) with 60 g of Scotchlite™ H50/10,000 EPX glass bubbles (available from 3 M Company, St. Paul, Minn.)

which had been dried by heating at 120° C. for about 16 hours until a dry to the touch putty-like consistency was obtained. The batch was split into 2 equal parts and each was placed in a Teflon mold, as described in Example 2, and rolled flat to fit the mold using a quart jar. A piece of cheese cloth which had been coated with resin as desecribed in Example 1 was sandwiched between the two sheets of composite and the laminate was placed in a Teflon mold and was rolled together using the quart jar. This article was then stored flat in a polyethylene coated aluminum foil pouch. The articles were comprised of the following parts as set out in Table 7b:

TABLE 7b

| Run # | Resin A (g) | Resin B (g) | Catalyst (%) | Bubbles (g) | $V_f/V_r$ |
|---|---|---|---|---|---|
| 1 | 21 | 22.4 | 1 | 63 | 2.95 |
| 2 | 0 | 44 | 1.2 | 66 | 3.04 |
| 3 | 41 | 0 | 1.2 | 61 | 3.01 |
| 4 | 40 | 0 | 0.8 | 60 | 3.06 |
| 5 | 0 | 43 | 0.8 | 65 | 3.09 |
| 6 | 25 | 27 | 1.0 | 78 | 3.06 |
| 7 | 21.73 | 20.0 | 1.0 | 61.8 | 3.01 |

Each article was then evaluated as follows: Water was put in a 1 gallon bucket at about 25° C. A 35 cm (approx.) piece of 5.08 cm stockinette (3M) was placed over a 5.08 cm steel mandrel. The article was dipped in water for exactly 10 and pulled out of the water. Each article was placed longitudinally on the and was rubbed by the applier to evaluate the extent of resin movement or "cream level" and handling properties for about 30 seconds, and then was overwrapped with an ace bandage.

The following properties were evaluated: set time, cream level, and relative initial cohesive strength. The results are listed below in Table 7c.

TABLE 7c

| Run | Set time (sec) | Cream level (rank 1 to 15) | Initial strength (rank 1 to 10) |
|---|---|---|---|
| 1 | 222.9 | 10.0 | 1.0 |
| 2 | 153.0 | 2.0 | 4.0 |
| 3 | 190.9 | 12.0 | 3.0 |
| 4 | 244.6 | 10.0 | 1.0 |
| 5 | 145.7 | 1.0 | 4.0 |
| 6 | 221.0 | 10.0 | 1.0 |
| 7 | 222.0 | 4.0 | 1.0 |

Set time was the time required for the composite to cure sufficiently to maintain its shape so that it could no longer be easily shaped by hand pressure.

Relative cream level was a subjective measurement of ease and extent of composite redistribution on the surface of the material. This parameter is ranked on a scale of 1 to 15 where 1 represents a material which is not creamy (i.e., the composition did not move on the surface) and 15 represents a material which has a plaster-like composite cream.

Relative initial cohesive strength is a subjective measurement on a scale of 1 to 10 where 1 represents a material which is very weak (i.e., falls apart during molding) and 10 represents a material which is as strong as commercially available fiberglass articles such as 3M Scotchcast® One-Step Splint measured about 10 minutes after dipping in water.

It is observed that the fastest set time was obtained with 100% Resin B and at higher concentrations of Resin A set time was increased. Cream level increased as percent Resin A increased. Initial strength decreased as percent Resin A increased (i.e., as the level of polyethylene glycol increased).

Example 8

Rheology of Resins Comprising Secondary Polymer

A series of eight resins were prepared in order to illustrate the effect of the addition of a soluble secondary polymer on the rheology of the resin and in particular on the tan δ of the resin. The rheology can be quantified by measuring the storage modulus, G', and the loss modulus, G", of the resin. As will become apparent from the examples, a material's rheology will be affected by both the concentration of secondary polymer added and the molecular weight of the secondary polymer.

Two different molecular weight PVP polymers were added to a water-curable resin as described below. The first series of resins were prepared using PVP-360. The PVP-360 was dissolved in Terathane 1000 at a concentration of 13.5% by weight according to the drying procedure of Example 2 to form a stock solution ("PVP-T"). Using this stock solution five modified resins were prepared according to the following formulation as described in Tables 8a and 8b:

TABLE 8a

| Chemical | Eqwt. (g/eq) | Weight (g) |
|---|---|---|
| PVP-T | | see below |
| Terathane 1000 | 490.0 | see below |
| Benzoyl chloride | | 0.16 |
| Antifoam 1400 | | 0.36 |
| BHT | | 0.96 |
| Isonate 2143L | 144.4 | 111.26 |

The PVP/Terathane solution and the Terathane 1000 were added according to the following table:

TABLE 8b

| Resin → | A | B | C | D | E |
|---|---|---|---|---|---|
| PVP-T solution (g) | 0 | 13.75 | 27.79 | 42.11 | 56.73 |
| Terathane 1000 (g) | 73.08 | 61.18 | 49.04 | 36.65 | 24.00 |
| Weight % PVP | 0 | 1 | 2 | 3 | 4 |

The resin was prepared by adding together the PVP-T solution and the Terathane to a 8 oz. jar (maintained at 49° C.) and mixing thoroughly. Next all of the components listed in Table 8a were added in the order listed with mixing for approximately 5 minutes between each addition. The final solution was vigorously shaken for 1 hour then placed in a 65° C. oven overnight to ensure the resin was bubble free. Note that these samples do not contain a catalyst. This was done to ensure the resin did not cure while rheology measurements were being taken. In addition, the rheometer's test chamber was continuously purged with nitrogen.

A second set of resins was prepared using 1,280,000 molecular weight PVP (available from ISP Technologies as "K-90" and hereinafter referred to as "PVP-1280"). The PVP-1280 was dried by adding 500 g PVP-1280 to 2000 g Carbowax 600. The mixture was placed under vacuum with stirring and heated to 145° C. at a pressure of 0.6 mm Hg.

This stock solution, "PVP-C," was held at 145° C. for 1.5 hours and then cooled to 49° C. The resins were prepared by mixing together the following resin components:

TABLE 8c

| Chemical | Eqwt. (g/eq) | Resin F | Resin G | Resin H |
|---|---|---|---|---|
| Isonate 2143L | 144.4 | 114 | 114 | 114 |
| PVP-C | | 40 | 58 | 116 |
| Carbowax 600 | 310.9 | 13 | 0 | 0 |
| Carbowax 1450 | 739.1 | 15.2 | 15.2 | 15.2 |
| Arcol LHT-240[1] | 237.0 | 14 | 14 | 14 |
| (Approx. wt. % PVP) | | 4 | 6 | 11 |

[1]Polypropylene glycol glycerol started triol.

The resins were prepared by mixing the PVP-C solution and Carbowax 600 (if used) into the Isonate 2143L and heating to between about 65 to 70° C. The contents were mixed vigorously until the PVP-1280 was uniformly distributed and a viscoelastic solution resulted. The remaining polyols were added in the order shown with vigorous mixing between additions. Once mixed the resins were sealed and placed in a 65° C. oven for 12 hours to ensure entrapped air bubbles were minimized. Resin H still had some aeration due to its extremely high viscosity. Note that these samples do not contain a catalyst. This was done to ensure the resin did not cure while rheology measurements were being taken. In addition, the rheometer's test chamber was continuously purged with nitrogen.

For purposes of the present invention, the rheology of the resins was determined using a Rheometrics Dynamic Analyzer (RDA-II) in parallel plate geometry. All experiments were done at 25° C. under a dry nitrogen environment in a dynamic shear mode where the dynamic strain was kept below the linear viscoelastic strain limit (i.e., less than 10%). The diameter of the plates was varied so as to keep the measured torque within the operating limits of the rheometer. The gap between the plates was less than about one mm. Both the storage modulus (G') and the loss modulus (G") were measured. The results indicate that over the shear range of 0.1–100 radians per second the storage modulus is increased by almost 3 orders of magnitude by addition of as little as 1% of the PVP-360 (resin B). Addition of 11% of the PVP-1280 increased the storage modulus by almost 7 orders of magnitude over the shear range tested. A complete listing of the data appears below in Table 8d.

A series of 7 curable resins were analyzed for yield stress and zero shear viscosity at 25° C. The first six resins (Resins B to G) correspond to duplicate batches of those resins disclosed above. Resin "I" had the following formulation and was prepared in the same method as resin G.

TABLE 8e

Preparation of Resin "I"

| Chemical | Eqwt. | Weight (g) |
|---|---|---|
| Isonate 2143L | 144.4 | 114 |
| PVP-C[1] | | 80 |
| Carbowax 1450 | | 15.2 |
| Arcol LHT-240 | | 14 |

[1]"PVP-C" = PVP/Carbowax 600 solution prepared per Example 8.

In a similar manner, viscosity versus shear rate data was generated using a Rheometric Dynamic Analyzer in parallel plate geometry over a range of shear rates (0.005 sec$^{-1}$ to 10 sec$^{-1}$). The zero shear viscosity was calculated from these curves using the following method. The shear stress at the onset of shear thinning was used as a starting stress for constant shear experiments in the Rheometrics Stress Rheometer. A constant stress was applied for 200 seconds, and the recoverable strain was monitored for 1000 seconds. If there was no recoverable strain, the stress was deemed to be too high and if there was 100% recoverable strain the stress was deemed too low. Using this trial and error method the proper stress was obtained. In addition, a stress ramp experiment was done using a stress range from 0–10,000 dyne/cm$^2$ for 1000 seconds. The lowest stress where a measurable strain was observed was defined as the yield stress. The results are listed in Table 8f.

TABLE 8f

| Sample | Yield Stress (dyne/cm2) | Zero Shear Viscosity (Pa s) |
|---|---|---|
| B | 10 | 12.5 |
| C | 15 | 55.0 |
| D | 35 | 118.0 |
| E | 40 | 156.5 |
| F | 600 | 842.0 |
| G | 16,000 | 18,500 |
| I | 18,000 | 41,200 |

TABLE 8d

| Resin | A | B | C | D | E | F | G | H |
|---|---|---|---|---|---|---|---|---|
| PVP conc. (~wt. %) | 0 | 1 | 2 | 3 | 4 | 4 | 6 | 11 |
| Mol. wt. (×1000) | — | 360 | 360 | 360 | 360 | 1,280 | 1,280 | 1,280 |
| G' at 0.1 rad/sec[1] | 0.009 | 1.8 | 14 | 28 | 100 | 850 | 2100 | 38,000 |
| G' at 1 rad/sec | 0.028 | 30 | 180 | 350 | 900 | 4,300 | 9,000 | 110,000 |
| G' at 10 rad/sec | 0.22 | 300 | 1,300 | 2,200 | 4,400 | 17,000 | 29,000 | 420,000 |
| G' at 100 rad/sec | 6 | 2,000 | 5,600 | 10,000 | 18,000 | 52,000 | 88,000 | 2,100,000 |
| G" at 0.1 rad/sec[2] | 1 | 20 | 75 | 150 | 350 | 1,700 | 3,000 | 40,000 |
| G" at 1 rad/sec | 9 | 180 | 580 | 900 | 1,800 | 6,000 | 10,100 | 170,000 |
| G" at 10 rad/sec | 98 | 1,020 | 2,900 | 3,000 | 7,500 | 25,000 | 40,000 | 700,000 |
| G" at 100 rad/sec | 950 | 7,000 | 13,000 | 20,000 | 30,000 | 120,000 | 190,000 | 3,000,000 |
| Tan δ[3] at 0.1 rad/sec | 111 | 11 | 5.4 | 5.4 | 3.5 | 2.0 | 1.4 | 1.1 |
| Tan δ at 1.0 rad/sec | 321 | 6.0 | 3.2 | 2.6 | 2.0 | 1.4 | 1.1 | 1.5 |
| Tan δ at 10 rad/sec | 445 | 3.4 | 2.2 | 1.4 | 1.7 | 1.5 | 1.4 | 1.7 |
| Tan δ at 100 rad/sec | 158 | 3.5 | 2.3 | 2.0 | 1.7 | 2.3 | 2.2 | 1.4 |

[1]Dyne/cm$^2$
[2]Dyne/cm$^2$
[3]Ratio of G"/G'

Example 9

Air Flow Through a Cured Composite

One advantage of the composites of the present invention is their relatively high porosity which allows the cast to "breathe" during wear. The breathability of a series of composites which were produced using various microspheres at different concentrations was characterized according to the following test.

A W. & L. E. Gurley Densometer Model 4110 (Troy, N.Y.) attached to a Gurley-teledyne sensitivity meter (Cat. No. 4134/4135—used for calibration) and an Engler Instruments Co. Model 605 timer was used to measure the flow of air through a composite specimen. Specifically, this instrument measured the time in seconds required to pass 10–50 cc of air through a 6.45 sq cm piece of 0.64 cm thick cured composite. The test was performed in a room having a temperature between 23 and 25° C. and about 50% relative humidity.

The samples were prepared in the following manner. In the center of both sides of a 5 cm×5 cm square piece of cured composite (0.64 cm thick) was adhered a 2.54 cm diameter circular piece of Microfoam tape (3M Company, St. Paul, Minn.). Next, the entire sample (top, bottom, and sides) was sealed using Dow Corning 732 RTV multipurpose silicone sealant (Midland, Mich.). The samples with sealant were allowed to cure overnight. Once cured the microfoam tape circles were gently removed using a tweezers to leave a 2.54 cm diameter circular opening through which air could be passed.

The top surface was then covered with a piece of Scotch Brand #471 yellow plastic tape (available from 3M Co., St. Paul, Minn.) which had a mating 2.54 cm diameter hole. Initially the bottom surface was covered with a piece of Scotch Brand #471 yellow plastic tape (without a hole therein).

The sample was then tested for its leak rate, i.e., the rate at which air leaked through imperfections in the seal and/or sealant layer. The leak rate ("L" in cc/sec) of the sample was determined by placing the sample in the Densometer and measuring the air flow, i.e., the time required to pass a known volume (e.g., 10 to 50 cc) of air. Next the lower occluded layer of tape was replaced with a layer of tape identical to that on the top of the sample except that a 2.54 cm diameter hole was cut and aligned with the sample hole. The air flow rate through the sample and sealant was measured as previously described ("F" in cc/sec). By subtraction the air flow through the sample was then determined by the following formula: actual sample air flow=F–L (cc/sec). The numbers reported below are an average of two samples. Preferably, an average of at least 5 samples is utilized.

Composite samples were prepared using the resin of Example 3. The resin was mixed with various fillers, using the procedure of Example 3 and as described in Table 9 to produce samples approximately 0.64 cm thick. The samples were immersed in 25° C. water and allowed to cure for at least 24 hours prior to testing. In addition, a commercially available 15 layer plaster splint (Orthopedic Casting Laboratories—without padding layers available from Worldwide Management Corp., Eudora KS) (Run #6) and an 6 layer slab of Scotchcast Plus Casting tape (Run #7) were tested. The following air flow results were found:

TABLE 9

| Run # | Filler | Weight % | Flow (cc/sec) | $V_f/V_r$ |
|---|---|---|---|---|
| 1 | 3M A16150 | 50 | 10.7 | |
| 2 | 3M A161500 | 55 | 14.5 | |
| 3 | 3M B3712000 | 55 | 13.2 | |
| 4 | 3M K-1 | 65 | 3.4 | |
| 5 | Dicaperl HP-900 | 67 | 7.7 | 6.40 |
| 6 | OCL Plaster | — | 0.04 | |
| 7 | 3M Scotchcast ™ Plus (6 layers) | — | 1028 | |

For materials with a high air flow value it may be necessary to either increase the volume of air passed, e.g., 300 cc, or decrease the surface area which is open to air flow. However, if the circular opening is reduced the air flow value must be corrected i.e., normalized to an equivalent air flow per unit area, prior to comparing samples. For example, if a sample was prepared with a 1.27 cm circular hole in place of the 2.54 cm circular hole described above the air flow obtained would be multiplied by 4 to yield a proper comparison.

Example 10

Rate of Dissolution of Various Water-Soluble Films

The time required to "dissolve" a water soluble film is characterized in accordance with the following test method. A single layer of film is cut and secured between the top and bottom halves of a Millipore Filter Holder (Part #4 but without its standard filter screen—Millipore Corp., Bedford, Mass.) to provide a 3.5 cm diameter piece of film secured in place. Twenty milliliters of water is gently added to the top of the fixture (creating approximately a 2 cm head atop the film) by pouring the water down the side of the fixture. The time for the water to dissolve the film and "break-through" the film (i.e., flow through the film) is recorded. Dissolution time is recorded as the mean break-through time of ten samples and is reported below in Table 10a.

TABLE 10a

| Run | Film | Thickness (micron) | Dissolution time (sec) Undried film | Dissolution time (sec) Dried film[4] |
|---|---|---|---|---|
| 1 | QSA 2004[1] | 38 | 12.5 | 24.9 |
| 2 | QSA 2004 | 51 | 23.5 | 50.3 |
| 3 | QSA 2000[1] | 38 | 21.3 | 47.2 |
| 4 | QSA 2000 | 51 | 37.0 | 96.1 |
| 5 | Aicello Solublon SA[2] | 17 | 2.7 | 3.7 |
| 6 | EM1100[3] | 53 | 22.3 | 49.9 |

[1]Available from Glenn Corp., St. Paul, Minn.
[2]Available from Mitsui Plastics Inc., White Plains, NY.
[3]Hydroxypropylmethylcellulose (CAS No. 009004-65-3) available from Glenn Corp., St. Paul, Minn.
[4]Dried for 20–24 hours at 100° C.

The above test yields a good approximation of the time required for dissolution of a film. However, as an alternative embodiment of the present invention one may choose to forego use of a separate film of liner and instead directly laminate the casting material with a water-soluble liner material. This liner film may be difficult, if not impossible, to later separate from the casting material and test in accordance with the above method. To test these liner materials it is acceptable to either employ a functional test (i.e., directly measure the casting tape under conditions of use and measure the time required for the liner to provide a lubricating effect or allow layer-to-layer adhesion of the casting material) or a modification of the above "breakthrough" test. For example, one may directly form the liner film against the millipore filter (with the same thickness as found on the casting material) and then conduct the breakthrough test. Alternatively, one may form the liner film against any other suitable porous substrate and place the laminate in the millipore apparatus for testing as described above.

Example 11

Moisture Vapor Transmission Through a Casting Material

The moisture vapor transmission of various casting materials is measured using the following test. A ring of casting material measuring between 5 and 10 cm high and having a 5.08 cm inner diameter is formed by curing the material against a stockinet covered mandrel. Alternatively, the ring may be formed by gluing together two fully cured half rings (i.e., "C" shaped sheets having an inner radius of 2.54 cm) using a water impermeable sealant. Prior to testing, the casting material is allowed to cure for 24 hours. The surface area of the cylinder (A) is taken as the inner circumferential area, less any areas (such as seam areas) which were occluded with sealant. The average thickness of the cast material is also recorded (T). For comparison purposes the average thickness of the casting material being tested should preferably be that thickness which provides a comparable ring strength (as described in column 15 of U.S. Pat. No. 4,705,840) to 6 layers of 3M Scotchcast™ Plus casting tape, i.e., approximately 90 N/cm width (±45 N/cm width).

The cylinder of cast material is then sealed completely around its lower circumference to a lower petri dish using a silicone sealant such as Silastic RTV silicone sealant No. 732 (available from Dow Corning Co., Midland Mich.). The sealant is allowed to cure for 24 hours. A 25 ml beaker of deionized water is placed inside the cylinder and on top of the lower petri dish. Care is taken to not spill the water from the beaker. The top of the cylinder is then closed by sealing a second petri dish on the top circumference using the aforementioned RTV sealant. The sealant is allowed to cure for 12 hours.

The total weight of cast material, petri dishes, beaker, and water is recorded. The samples are then placed in a 37.8° C. oven having a relative humidity of between 24 and 30 percent. The samples are removed periodically and weighed. The weight loss per unit time is calculated as the slope of the weight loss vs. time plot. The slope may be calculated using a least squares line fitting method if desired. The results are expressed as the slope of the weight loss vs. time divided by the area, A, of the cast material. The "moisture vapor transmission" is expressed in units of g water lost/day/sq cm.

The seven samples described in Example 7 along with the three samples described in Example 14 were tested for moisture vapor permeability. These samples were compared to a traditional plaster of Paris material and a traditional synthetic fiberglass material. The plaster of Paris material was Synthetic Plus™ Plaster (cat. no. 4900-03 available from Depuy Co., Warsaw, Ind.). The fiberglass material was Scotchcast™ Plus (available from 3M Co., St. Paul, Minn.). For the fiberglass and Plaster samples two replicates were run. For the samples of this invention only one sample was available. Preferably an average of 3 to 5 samples would be recorded.

TABLE 11a

| Run | Sample | Vapor transmission (g water lost/day/sq cm) |
|-----|--------|---------------------------------------------|
| 1 | Example 7 run 1 | 0.196 |
| 2 | Example 7 run 2 | 0.253 |
| 3 | Example 7 run 3 | 0.248 |
| 4 | Example 7 run 4 | 0.160 |
| 5 | Example 7 run 5 | 0.178 |
| 6 | Example 7 run 6 | 0.176 |
| 7 | Example 7 run 7 | 0.201 |
| 8 | Scotchcast Plus (6 layers) | 0.413 |
| 9 | Plaster: Synthetic Plus ™ Plaster (Depuy)(15 layers) | 0.185 |
| 10 | Example 14 run 1 | 0.110 |
| 11 | Example 14 run 2 | 0.195 |
| 12 | Example 14 run 3 | 0.268 |

Example 12

Strength Testing—Three Point Bend and Tensile Methods

The flexural strength and modulus of several materials of the present invention were compared to two traditional casting materials (plaster of Paris and a synthetic fiberglass casting material). As shown below in Table 12d the materials of the present invention compare favorably to these traditional materials. In order to make this comparison samples were prepared and tested for flexural strength and flexural modulus using a modified version of ASTM test method number D790-91 entitled: "Standard Test Methods for Flexural Properties of Unreinforced and Reinforced Plastics and Electrical Insulating Materials".

Seven resin compositions were made which had varying amounts of a secondary polymer component (of varying molecular weights) as described in Tables 12a and 12b. To these resins were added glass bubbles (Scotchlite™ H50/10000 EPX) at a concentration of 60 percent by weight filler. The composite materials ($V_f/V_r$=3.1) were made into splints according to the general procedure of Example 7.

TABLE 12a

| Chemical | Eqwt. (g/eq) | Resin A | Resin B | Resin C |
|----------|--------------|---------|---------|---------|
| Isonate 2143L | 144.4 | 228 | 228 | 228 |
| Secondary polymer solution[1] | | 132.5 | 88.0 | 45.0 |
| Carbowax 600 | 301.9 | 0 | 35.4 | 70.0 |
| Carbowax 1450 | 739.1 | 30.4 | 30.4 | 30.4 |
| Arcol LHT-240 | 237.0 | 28.0 | 28.0 | 28.0 |
| Benzoyl Chloride | | 0.2 | 0.2 | 0.2 |
| Antifoam 1400 | | 0.72 | 0.72 | 0.72 |
| BHT | | 1.92 | 1.92 | 1.92 |
| MEMPE | | 4.8 | 4.8 | 4.8 |

[1]20% by weight solution of either: PVP-360 (having 360,000 molecular weight and available from Aldrich Chemical Co.); PVP-1280 (having 1,280,000 molecular weight and available from ISP Technologies) dissolved in Carbowax 600 (available from Union Carbide Co.); or a 1:1 blend of these solutions as described in Table 12b.

TABLE 12b

| Resin No. | Resin | Secondary polymer |
|-----------|-------|-------------------|
| 12-1 | A | PVP-360 |
| 12-2 | C | PVP-360 |
| 12-3 | B | 1:1 Blend of PVP-360 and PVP-1280 |
| 12-4 | B | 1:1 Blend of PVP-360 and PVP-1280 |
| 12-5 | A | PVP-1280 |

TABLE 12b-continued

| Resin No. | Resin | Secondary polymer |
|---|---|---|
| 12-6 | B | 1:1 Blend of PVP-360 and PVP-1280 |
| 12-7 | C | PVP-1280 |

In addition, several splints were made using the resin described below in Table 12c (hereinafter referred to as Resin 12–8) and 65% by weight Scotchlite™ H50/10000 EPX glass bubbles (3M Company), resulting in a composite having a $V_f/V_r=3.9$.

TABLE 12c

| Chemical | Eqwt. (g/eq) | Weight (g) |
|---|---|---|
| Isonate 2143L | 144.4 | 228 |
| PVP-Carbowax 600[1] | | 122.5 |
| Carbowax 1450 | 739.1 | 30.4 |
| Arcol LHT-240 | 237.0 | 28.0 |
| Benzoyl Chloride | | 0.2 |
| Antifoam 1400 | | 0.72 |
| MEMPE | | 4.8 |

[1] 13.5% by weight solution of PVP-360 (available from Aldrich Chemical Co. and having a 360,000 molecular weight) dissolved in Carbowax 600 (available from Union Carbide Co. and having an equivalent weight of 301.9 g/eq).

The splints were made in an atmosphere of less than 4% relative humidity by rolling the fully homogenous composition into a 9.53×30.5×0.635 cm teflon mold. No scrim was placed in the materials. The composite splints were stored flat in sealed aluminum foil pouches until use.

The splints were evaluated during the cure process. All samples were observed to provide acceptable splinting materials and had set times between 136 and 214 seconds. In general, samples which contained higher molecular weight secondary polymer and higher concentrations of secondary polymer exhibited higher cohesive strength.

The samples were cured by immersion in 25° C. water followed by molding the materials as a flat sheet or laminate and then storing the materials at 25° C. and 50% relative humidity. Each material was immersed in the water for 10 seconds without agitation. For the sheet materials of the present invention the material was simply allowed to cure in a flat state. For the plaster of Paris sample (OCL Roll Form Splint, 15 layers of plaster) the outer padding was first removed. The fiberglass sample (Scotchcast™ Plus available from 3M Co., St. Paul, Minn.) was formed into 6 and 8 layer laminates. Once removed from the water, the plaster of Paris and fiberglass samples were compressed slightly by hand and rubbed to promote layer to layer lamination. Preferably, a minimum of 5 samples were tested and the mean reported. However, in some cases only 2 samples were tested. Once cured the samples were cut to 9.53 cm long strips. The width of the samples of the present invention were 9.6 cm. The width of the 3M Scotchcast Plus samples were 8.5 cm. The width of the plaster of Paris samples were 6.86 cm. The samples were allowed to cure overnight in a room maintained at 25° C. and 50% relative humidity prior to testing for strength.

The flexural strength and flexural modulus values for these samples are listed in Table 12d. Sample numbers 12-3 and 12-7 were not tested. Each sample was placed in a fixture and the fixture properly centered in a properly calibrated Instron™ 1122 testing machine (Instron Corp., Park Ridge, Ill.). The fixture was a three point bend device in which the supports were cylindrical rods (1.91 cm in diameter and 13.7 cm long). The supports were parallel to one another and spaced 7.62 cm apart (measuring from the centerline). The load was applied through a similar cylinder positioned above the sample at the midpoint of the support cylinders. Compression loads were applied to the flat sample at the midpoint of the sample using a crosshead speed of 2.54 cm per minute.

The flexural strength ("S") was calculated using the following formula: $S=3FL/2bd^2$ where: F=maximum load (N); L=support span (in this case=7.62 cm); b=width of sample (cm); and d=sample thickness (cm). The flexural modulus ("$E_b$") was calculated using the following formula: $E_b=m(L^3/4bd^3)$ where, L, b, and d are as defined above and m is the slope of the load displacement curve.

TABLE 12d

| Sample No. | Flexural strength (N/cm$^2$) | Flexural modulus (N/m$^2$) |
|---|---|---|
| 12-1 | 1006 | 10.5 |
| 12-2 | 824 | 5.64 |
| 12-4 | 1837 | 10.2 |
| 12-5 | 1764 | 7.42 |
| 12-6 | 976 | 4.00 |
| 12-8 | 918 | 5.20 |
| Plaster-15 layers | 1199 | 11.7 |
| 3M Scotchcast Plus - 8 layers | 655 | 1.94 |
| 3M Scotchcast Plus - 6 layers | 1172 | 7.95 |

Two uncured samples were prepared in the form of 25.4 mm wide sheets and tested for their tensile strength. Samples were conditioned in a sealed package at 23–25° C. for at least 24 hours prior to testing. Each sample was placed in the pneumatic jaws of a properly calibrated Instron 1122 testing machine (Instron Corporation, Park Ridge, Ill.) equipped with Sintech Test Works™ material testing software (Sintech, Stoughton, Mass.). The jaws were equipped with a metal spacer to prevent crushing of the sample (i.e., the sample should be held by the jaws with enough force to resist slippage during testing but not so much force that the uncured material is crushed to the point of breaking. The jaw spacing was 2.54 cm and the samples tested were 2.54 cm wide×7.62 cm long and were cut from length direction of the casting material such that the tensile direction corresponded to the direction in which the principle load would be applied during actual application of the products. The crosshead speed was set at 2.54 cm/min. Peak load to failure per unit width of sample is reported below in Table 12e. All materials were tested immediately after removal from the storage pouch, i.e., before being cured and without dipping in water. Preferably an average of at least 5 samples is reported.

TABLE 12e

| Sample No. | Tensile strength (N/mm) |
|---|---|
| 12-2 | 0.149 |
| 12-7 | 0.119 |
| Cheese cloth | 0.520 |
| Plaster of Paris | 0.870 |

Example 13

Bulk Density of a Filler

The bulk density of several fillers was measured according to the following test method. A 25 ml graduated cylinder was filled with the filler sample and vibrated lightly for 5 minutes. After this time the volume of filler (i.e., as read from the graduations on the side of the cylinder) was recorded. The weight of filler was determined by subtracting the weight of the cylinder from the total weight of the cylinder and filler. The bulk density is reported as the weight/unit volume of filler (g/cc).

Example 14

Void Volume Measurement

The void volume of a cured composite was determined by the following test method. A sample of a cured composite of known volume ("$V_c$") and weight ("$W_c$") is fully submerged in a pan containing a solvent. Suitable solvents for this purpose include solvents which have a relatively low surface tension yet do not cause rapid swelling, dissolution, or disintegration of the composite. In this example isopropyl alcohol ("IPA") was found to be suitable and was used. The sample is submerged in the solvent using any suitable device (such as a small weight) and then placed in a vacuum chamber. In this example a 73 g weight was used to submerge a sample measuring approximately 10.16 cm×8.89 cm×0.635 cm. Care was taken to minimize the area of contact between the weight and sample so as to not prevent absorption of the solvent into the sample.

The submerged sample was placed in a vacuum chamber and a vacuum was pulled to a pressure of 125 mm Hg. The vacuum was held for approximately 2 minutes, however, longer times may be necessary to ensure complete absorption of the solvent into the sample's pores. The sample was removed from the chamber and residual solvent was removed by quickly blotting the sample with a Premiere™ (Scott Paper Company, Philadelphia Pa.) paper towel. The weight of the IPA impregnated sample ("$W_{cs}$") was then recorded. Preferably at least 5 samples are analyzed and the mean absorption weight is calculated. The weight of absorbed solvent ("$W_s$") is calculated by subtraction ($W_s$ equals $W_{cs}$ minus $W_c$) and converted to volume ("$V_s$") using the density relationship for that solvent (i.e., 0.785 gm/ml for IPA). The volume of absorbed solvent (i.e., the void volume of the composite) is then expressed as a ratio of the volume of the cured composite ($V_s/V_c$) or as a percentage of the volume of the cured composite (% void volume equals 100 times ($V_s/V_c$)).

The void volume was measured on three cured composite materials. The materials were formed into 30.5 cm×8.9 cm×0.64 cm slabs using the resin described in Table 14a and various levels of 3M H50/1000 EPX glass bubbles as described in Table 14b and then cut to a length of 10.16 cm for testing. The resin and splints were made according to the general procedure of Example 7. Notably, the composite's volume did not significantly change during cure.

TABLE 14a

| Chemical | Eqwt. (g/eq) | Weight (g) |
| --- | --- | --- |
| Isonate 2143L | 144.4 | 228 |
| Secondary polymer solution[1] | | 122.5 |
| Carbowax 1450 | 739.1 | 30.4 |
| Arcol LHT-240 | 237.0 | 28.0 |
| Benzoyl Chloride | | 0.2 |
| Antifoam 1400 | | 0.72 |
| MEMPE | | 4.8 |

[1]13.5% by weight solution of PVP-360 (available from Aldrich Chemical Co. and having a 360,000 molecular weight) dissolved in Carbowax 600 (avaiable from Union Carbide Co. and having an equivalent weight of 301.9 g/eq).

TABLE 14b

| Sample | Filler (g) | Filler (bulk vol) | Resin (g) | Vol. Uncured Composite (ml) | Void vol. (%) | $V_f/V_r$ |
| --- | --- | --- | --- | --- | --- | --- |
| 14-1 | 60 | 194 | 40 | 195 | 19.7 | 3.12 |
| 14-2 | 65 | 216 | 35 | 215 | 24.5 | 3.86 |
| 14-3 | 70 | 295 | 30 | 220 | 24.0 | 4.85 |

Example 15

Composite Comprising a Thermoplastic Binder

A solution of Tone 787 polycaprolactone polymer (available from Union Carbide and reported to have a molecular weight of 80,000) was made by dissolving 220 g polymer in 500 g toluene and gently agitating for 24 hours. After this time an additional 75 g toluene was added and mixed and the contents warmed to 65° C. to produce a clear viscous solution which contained 28% by weight polycaprolactone.

In a one liter beaker containing 45 g Scotchlite™ H50/1000 glass bubbles (3M Co., St. Paul, Minn.) was added 85.7 g of the above solution. This was initially mixed using a tongue depressor and then later kneaded by hand. As the material became tacky an additional 16 g bubbles were added and the mixture kneaded. The final composition was only slightly tacky. This was rolled into a 7.6 cm×30.5 cm×0.64 cm mold and set in a fume hood for several hours to allow the toluene to begin evaporating. The material was then placed in a 48° C. oven for approximately 14 hours to ensure all the toluene had evaporated.

A smooth porous composite resulted. The void volume was measured according to the method in Example 14 and found to be 34.65%.

The material was immersed in a 70° C. water bath for 5 minutes and molded around a wrist. The material was observed to be very conformable. The cast's strength was just adequate for immobilization of a wrist but would be suitable for lower load applications such as finger splints and the like.

Example 16

Composite Comprising a Thermoplastic Binder

A solution 31 percent by weight Tone 787 in toluene was produced by mixing 220 g Tone into 490 g toluene and mixing gently for 24 hours (Solution "16A"). The solution was heated to 65° C. for 7 hours to form a clear viscous homogenous solution. The polymer solution was mixed with glass bubbles, formed into a mold, and the toluene evaporated as described in Example 15. The following amounts of filler and polymer solution were used:

TABLE 16a

| Sample | Solution 16A (g) | Filler (g) |
| --- | --- | --- |
| 16-1 | 90 | 45.5 |
| 16-2 | 90 | 56.6 |

Notably both samples were observed to be quite tacky and were poured into the molds. The materials were allowed to sit for several minutes prior to rolling to allow residual toluene to evaporate.

After allowing for complete evaporation of the solvent the materials were pressed into a 0.5 cm thick slab using a heated Dake flat platten press (Model 44–027, Dake Inc. Grand Haven Mich.). The plattens were heated to 77° C. The samples were placed between two pieces of silicone coated release liner and pressed under very low pressure for approximately 1 minute to allow the sample to heat up. The pressure was then increased to approximately 4000 psi and released. Next both sides of the hot sample were dusted with additional glass bubbles and the material pressed again in the same manner but this time only to a pressure of approximately 1000 psi. The additional glass bubbles on the outer surface allowed the slab to be heated on a hot plate to a molten condition without sticking to the hot plate.

The samples were applied to a wrist by heating the sample in a warm water bath. Both samples B and C were molded to a wrist and had sufficient integrity to be used as a splint immobilization device.

To 40 grams of each resin was added 60 grams of 3M Scotchlite™ H50/10,000 EPX glass bubbles. A homogeneous composite was obtained ($V_f/V_r$=3.1(by kneading the filler into the resin by hand for several minutes. Each of the composites were formed into 0.6 cm thick sheets approximately 7.6×30 cm by use of a hydraulic press with 0.6 cm spacers. A maximum pressure of 52MPa was used to make the sheets. The sheets were sealed in water impervious aluminum foil pouches until use. The sheets were removed from the pouches and immersed in a water bath for 5 seconds and placed over a mandrel. The composite from resin formulation A was very soft and moldable while the composite from resin formulation B was very creamy and had a consistency approaching that of plaster. The composite from resin formulation C was extremely creamy and moldable and was fluid-like similar to plaster of Paris. All materials hardened after several hours to give rigid splints.

TABLE 17a

| Chemical | A (NCO/OH) = 3.1 | B (NCO/OH) = 3.5 | C (NCO/OH) = 3.9 |
|---|---|---|---|
| Isonate 2143L | 217 | 228 | 239 |
| Benzoyl Chloride | 0.26 | 0.26 | 0.26 |
| DB-100 | 0.66 | 0.66 | 0.66 |
| BHT | 1.76 | 1.76 | 1.76 |
| MEMPE | 5.12 | 5.12 | 5.12 |
| Carbowax 1450 | 50 | 46 | 43 |
| Carbowax 600 | 60 | 51 | 44 |
| Secondary polymer solution[1] | 83 | 83 | 83 |

[1]The secondary polymer solution is a 20% by weight solution of polyvinylpyrrolidone (available as "K-90" from ISP Technologies Inc., New Milford, CT) in Carbowax 600. This solution was prepared as follows: 729 grams of K-90 PVP was added to 2800 grams of Carbowax 600 at 40° C. in a 5 liter round-bottom flask fitted with a thermometer and overhead stirrer. A vacuum of 1 mm Hg was applied as the temperature was gradually raised to 110° C. This temperature was maintained for 4 hours until bubbling had ceased. The highly viscous liquid was then poured while still warm into four liter jars and stored in a 49° C. oven.

Example 17

Composite Comprising Resin Having Increased NCO/OH Ratio

Three resins were prepared in 454 ml glass jars using the following components in grams:
The secondary polymer solution is a 20% by weight solution of polyvinylpyrrolidone (available as "K-90" from ISP Technologies Inc., New Milford, Conn.) in Carbowax 600. This solution was prepared as follows: 729 grams of K-90 PVP was added to 2800 grams of Carbowax 600 at 40° C. in a 5 litre round-bottom flask fitted with a thermometer and overhead stirrer. A vacuum of 1 mm Hg was applied as the temperature was gradually raised to 110° C. This temperature was maintained for 4 hours until bubbling had ceased. The highly viscous liquid was then poured while still warm into four litre jars and stored in a 49° C. oven.

Resins "A", "B", and "C" were prepared according to the following general procedure. The 20% PVP/Carbowax 600 solution and the Isonate were mixed and gently heated with a heat gun and placed in a mechanical shaker for approximately 10 minutes until they became homogenous. Next the BHT, benzoyl chloride, and DB-100 were added and shaken for an additional 5 minutes in the mechanical shaker. The Carbowax 600, Carbowax 1450, and MEMPE were then added to the jars and laced in the shaker for another 10 minutes. The jars were placed in a 65.6° C. oven or 45 minutes, capped, and rolled slowly for several hours.

Example 18

Thin Sheet Composite Comprising PVP Modified Resin

A solution (designated as part "D") was prepared by mixing 328 grams of Isonate 2143L, 0.72 grams benzoyl chloride, 1.02 grams DB-100, and 2.76 grams of BHT in a one litre glass jar. A second solution (designated as part "E") was prepared by mixing 24 grams of undried PVP (available as "K-120" from ISP Technologies, Inc.) and 153 grams of warm Carbowax 600 in a one litre glass jar and placing the jar in a 65.6° C. oven for 2.5 hours. To this mixture was added 44 grams of Carbowax 1450 and 40 grams of Arcol LHT-240. The jar was placed in a mechanical shaker for 5 minutes then placed back in the oven for 30 minutes. 6.6 grams of MEMPE was added and the jar placed in the mechanical shaker for an additional 2 minutes then stored in the 65.6° C. oven.

A resin was made by mixing 139 grams of part D with 111 grams of part E in a 1 litre beaker. This mixture was stirred thoroughly using a high shear mixer (Premier Mill Corp., Reading, Pa.) for approximately 3 minutes. An exotherm was observed as well as some gas evolution indication possible chain extension of the prepolymer. 200 grams of this resin was placed on 300 grams of K-46 glass bubbles (having a specific gravity of 0.46 and available as Scotchlite™ from 3M Co.) in a 4.5 litre metal mixing bowl and a composite was formed by mixing with a Hobart mixer fitted with a sigma blade for approximately 5 minutes. The composite ($V_f/V_r$=3.4) was then formed into a flat rectangle and placed in a nip roller (comprising adjustable dual-driven rubber coated rollers having a 5 cm diameter and being 30.4 cm long) until a sheet 8.25 cm by about 3.8 cm was formed. The composite was pressed further to 0.15 cm thickness by passing it several times through a pasta maker (Atlas™, OMC Marcato Co., Campodarsego, Italy). Finally, the composite sheet was pressed through the pasta maker at a 0.127 cm gap with a porous polyester knit mesh fabric (style 6302 from Gehring Textiles, Inc., New York, N.Y.) of like dimensions. This tape was then rerolled on a plastic core and stored in a water-proof pouch until use. For evaluation as a casting tape the roll was then immersed in a 23° C. water bath for 10 seconds and rolled around a mandrel. The material unwound easily and was easily molded. Upon hardening the tape provided a rigid cast.

Example 19

Use of Isooctyl Acrylate/N-vinylpyrrolidone Copolymers in a Composite Tape

An isooctylacrylate and N-vinyl-2-pyrrolidone copolymer was produced according to the following procedure. To a 1 litre narrow-mouthed bottle was added 275.0 grams ethyl acetate, 168.75 grams isooctyl acrylate, 56.25 grams N-vinyl-2-pyrrolidone, and 0.3375 grams az deoxygenated by purging the bottle for two minutes with nitrogen at a flow rate of one liter per minute. The bottle was sealed and placed in a rotating water bath to effect essentially complete polymerization. Additional solvent (100 gm MeOH and 100 gm ethyl acetate) was added to produce a 30% solids solution. A 1000 gram aliquot of the above copolymer (comprising a 3:1 weight ratio of IOA to NVP) at 30% solids in ethyl acetate/methanol was stripped of solvent by first adding 900 grams of PPG 725 in a 3 litre flask fitted with a thermometer and condenser. The contents were heated to 125° C. for several hours and the solvent collected. The last traces of solvent were removed under vacuum (1–2 mm Hg) at room temperature for 16 hours. This gave a final solution that was 25% IOA/NVP in PPG 725. A solution (designated as part "F") was prepared by adding to a 4.5 litre jar 2730 grams of Isonate 2143L, 4.8 grams of benzoyl chloride, 8.7 grams of DB-100, and 23.1 grams of BHT. A second solution (designated as part "G") was prepared by mixing 60 grams of PPG 2025, 116 grams of PPG 725, 85.5 grams of LHT-240, and 361 grams of the IOA/NVP/PPG 725 solution from above. The mixture was placed in a 65.6° C. oven for 10 minutes, then placed in a mechanical shaker until it became homogeneous. To this solution was added 15.6 grams of MEMPE and the mixture was agitated for an additional 10 minutes.

In a dry room was mixed 147 grams of part F with 128 grams of part G in a 1 litre beaker with a hand-held electric mixer (Handy Mixer™, Black and Decker, Shelton, Conn.) for 3 minutes at high speed. 245 grams of this mixture was poured onto 300 grams of K46 3M glass bubbles (pre-dried in an oven at 125° C. for 3 days) in a 4.5 litre metal mixing bowl. The mixture was then made homogeneous by mixing with a Hobart mixer fitted with a metal sigma blade for 2 minutes. The composite ($V_f/V_r$=2.8) was stored in a water-proof pouch overnight until use. The next day a portion of the composite was calendered into approximately 0.254 cm thick sheets using a nip roller (comprising adjustable dual-driven rubber coated rollers having a 5 cm diameter and being 30.4 cm long. The resulting 7.6 cm by 1.8 m sheet was laid out on a table, dusted lightly with K-46 glass bubbles, and the surface lightly pressed with the edge of a tongue depressor (14.6×1.7 cm, Baxter Healthcare Corp., McGaw Park, Ill.) across the width of the tape approximately 1 cm apart and to a depth of about 0.12 cm. The sample was then rerolled and stored in a water-proof proof pouch until use. For evaluation as a casting tape, the sheet was removed from the pouch, immersed in 23° C. water for 10 seconds, and wound around a mandrel. The material was found to be wetted thoroughly throughout the roll. In addition, the material could be stretched, had good integrity, and was very moldable. The composite hardened in 5 minutes to give a rigid cast.

Example 20

Composite Tape Comprising a Light-weight Scrim

In a 1 litre beaker was added 147 grams of part F and 128 grams part G (both from example 19). The solution was mixed vigorously for 3 minutes using a high shear mixer, then poured over 300 grams of pre-dried K-46 glass bubbles. The material was homogenized using a Hobart mixer as described in example 19. At this point, the composite ($V_f/V_r$=2.5) had little integrity. Portions of it were sprinkled onto a 8.25 cm wide scrim of a light-weight web (comprising 1.75 denier polyester staple fibers 3.8 cm in length at 6 grams/m² coated with Roplex B15 resin from Rohm & Hass Co. at 2 grams/m²). The web with composite was then calendered through a nip roller (comprising steel rollers having a 7.6 cm diameter and being 22 cm long and coated with a PC-915 plasma coating, Plasma Coating Co., Bloomington, Minn.) with another layer of web so that the resulting composite was sandwiched evenly between the two layers of web. The resulting sheet, approximately 0.15 cm thick, was rerolled, and stored in a water-proof pouch until use. For evaluation as a casting tape, the roll was immersed in a 23° C. water bath for 10 seconds while water was squeezed into the roll. The material was then wound around a mandrel. The material was very conformable and moldable and gave a rigid cast in 10 minutes.

Example 21

Composite Tape Comprising a Hydrophilic Polyol and Exhibiting Increased Smoothability A solution (designated as part "H") was prepared by mixing 320 grams of a secondary polymer solution (described below) with 167 grams of Carbowax 600 in a 2 litre jar and placing it in a mechanical shaker until it became homogeneous. 121.5 grams of Carbowax 1450 was added and homogenized by shaking followed by 112 grams of Arcol LHT-240 and 21 grams of MEMPE. The mixture was placed in a 65.6° C. oven for 45 minutes, agitated in the mechanical shaker for 15 minutes, then stored in a 48.9° C. oven for later use. The secondary polymer solution was prepared by heating a mixture of 3020 grams of Carbowax 600 and 786 grams of PVP K-90 in a 5 litre flask at 1–2 mm Hg for 16 hours with gentle stirring.

A second solution (designated as part "I") was prepared by mixing 20 grams of PPG 2025, 69.5 grams of PPG 725, 28.5 grams of Arcol LHT-240, 5.2 grams of MEMPE, and 85 grams of a 30% IOA/NVP/PPG 725 solution in a 454 ml jar. The solution was homogenized using a mechanical shaker and stored in a 49° C. oven. The 30% IOA/NVP/PPG 725 solution was prepared by adding 700 grams of PPG 725 to 1000 grams of a 30% IOA/NVP copolymer in ethyl acetate/ methanol to a 2 litre flask. The majority of the solvent was distilled off at 125° C., and the residual solvent removed under a vacuum of 2 mm Hg.

A resin was prepared by mixing 92 grams of part F from example 19 with 40 grams of part I polyol solution from above and 28 grams of part H polyol solution from above for three minutes in a 500 ml beaker. 149 grams of this resin material was mixed in a Hobart mixer with 300 grams of H50/10,000 EPX glass bubbles forming a homogeneous composite. The composite ($V_f/V_r$=4.2) was then calendered to 0.23 cm thickness by repeatedly passing it through a rubber coated nip roller giving a sheet about 8.25 cm by 1.8 m. The sheet was dusted with Talcum powder, rerolled, and stored in a moisture-proof pouch until use. For evaluation as a casting tape, the roll was immersed in a 23° C. water bath for 5 seconds and rolled around a mandrel. The composite was sufficiently creamy and cured to give a rigid cast.

Example 22

Casting Tape

A resin was prepared by mixing in a 1 litre beaker 170 grams of part F (from example 19) with 83 grams of part H (from example 21) and 22 grams of a part "J" solution that was prepared according to the following procedure. In a one litre jar was added 60 grams of PPG 2025, 143 grams of PPG 725, and 348 grams of a 30% solution of IOA/NVP copolymer in PPG 725 (from example 21). The jar was shaken for 5 minutes, then 85.5 grams of Arcol LHT 240 and 15.6 grams of MEMPE were added. The jar was shaken for an additional 10 minutes, then placed in a 49° C. oven for 30 minutes. The warmed components were then mixed with a high shear mixer for 1 minute. 245 grams of the resulting homogeneous resin was poured onto 300 grams of K-46 glass bubbles in a 4.5 litre metal mixing bowl. The contents were mixed using a Hobart mixer with a sigma blade for approximately 3 minutes until the composite ($V_f/V_r$=2.8) became homogeneous.

A portion of the material was calendered to approximately 0.32 cm=2.8) thickness by repeated pressing between two rubber coated rollers. The composite was taken down further to about 0.18 cm thickness by running it through a pasta maker to give a sheet approximately 7 cm by 2.7 m. The sheet was then pressed between two layers of web (as described in Example 20) of like dimensions using the pasta maker to provide a tape of 0.14 cm thickness. The sheet was rerolled without a core and sealed in a moisture proof pouch until use. For evaluation as a casting tape, the roll was removed from the pouch, immersed in a 23° C. water bath for 15 seconds, then wound around a mandrel. The material was sufficiently creamy to allow for molding the material, felt soft to the touch, and cured to give a rigid cast in 10 minutes.

Example 23

Alternative Application of Composite to Scrims

A small portion of the composite of Example 22 was put through the "spaghetti" making portion of the pasta maker to give long cords of the composite about 0.635 cm wide and 0.25 cm thick. The cords of composite were longitudinally laid on top of the web of Example 20 (8.25 cm by 1 m) using 6 cords across the width of the scrim. Another sample of web of like dimension was placed on top of the composite and the material was pressed together by rolling the material with a metal knurled roller (7.6 cm diameter by 18 cm long with ridges running the length of the roll about 0.1 cm deep, 0.2 cm wide and 0.85 cm apart). The cords of composite sandwiched between two layers of scrim were then pressed through the pasta maker to provide a 0.18 cm thick tape. The tape was rerolled and stored in a moisture proof pouch until use. For evaluation as a casting tape, the sample was removed from the pouch, immersed in a 23° C. water bath for 5 seconds, and rolled around a mandrel. Water penetration into and throughout the roll was excellent. In addition, the material was creamy and was easily molded to give a rigid cast in 10 minutes.

Example 24

A Moldable Casting Tape

Preparation of Premix A-24: To a 1 liter jar under a nitrogen atmosphere was added 984 grams of Isonate 2143L, 2 grams of benzoyl chloride, 3 grams of DB-100, and 7.6 grams of butylated hydroxytoluene. The contents were mixed in a mechanical shaker for 10 minutes and stored at room temperature in a sealed jar.

Preparation of Premix B-24: To a 1 liter glass jar under a nitrogen atmosphere was added 365 grams Carbowax 600, 174 grams of LHT-240, 48 grams of Pluronic F-108, 12 grams of MEMPE, and 17 grams of a 45% by weight solution of an IOA/NVP (75/25) copolymer in PPG 725. The jar was placed in a oven at 65.6° C. for 16 hours and placed in a mechanical shaker for 10 minutes until it became homogeneous. The premix B was stored at 65.6° C. until ready for use.

Preparation of the Composite and Article: The following was done in a dry room kept at less than 5% humidity. To a 250 mL tripour beaker was added 112 grams of Premix A-24 and 78 grams of Premix B-24 and the mixture stirred by hand with a wooden tongue depressor for 3 seconds. Next, 170 grams of this partially reacted resin was added to a 454 ml jar containing 30 grams of Si 35/34 filler. The contents were mixed until homogeneous by first shaking by hand and then stirring with a rubber spatula.

A 7.6 cm×2.7 m piece of cheesecloth scrim (9.1×7.9 openings per cm) was fed between a knife and bed of a steel knife coater with the knife set to provide a gap of 0.031 cm. The composite was quickly poured onto a small portion of the scrim behind the knife and the scrim was coated with composite by pulling it through the gap at a rate of approximately 15.24 cm/sec. The surface of the coated scrim was then lightly dusted with K-46 glass bubbles by feeding the scrim around a horizontal roller that was immersed in a reservoir containing K-46 glass bubbles. The article was then rolled around a porous plastic core, stored in an aluminum foil pouch, and the pouch placed in a oven at 65.6° C. for 2 hours.

Preparation of a Cast: After the pouch had cooled to room temperature, the article was removed, dipped in a 23° C. water bath at for 5 seconds, and wound around a 5.1 cm diameter mandrel. The article was extremely moldable and cured to provide a very smooth, rigid cast in less than 30 minutes.

Example 25

Effect Of Filler Loading On Resin "Pooling"

To a 250 mL tripour beaker was added 124 grams of Premix A-24 (prepared as described above) and 76 grams of Premix B-24 (prepared as described above) and the mixture stirred with a tongue depressor for 3 seconds. Next, a portion of this resin was poured into a 454 ml glass jar that contained the Sil 35/34 filler. The jar was shaken by hand for 1 minute then coated on three 7.6 cm×2.7 m pieces of cheesecloth scrim as described above in Example 24. The following samples were prepared:

TABLE 25a

| Run No. | Resin (gm) | Filler (gm) | Ave. Coating Wt. (g/m$^2$) | $V_f/V_r$[1] |
|---|---|---|---|---|
| 1 | 200 | 0 | 278 | 0.00 |
| 2 | 190 | 10 | 224.2 | 0.22 |
| 3 | 180 | 20 | 219.3 | 0.46 |
| 4 | 170 | 30 | 224.2 | 0.73 |
| 5 | 160 | 40 | 219.3 | 1.04 |

One drop of Reactint Red X52 (Miliken Chemical Co., Spartanburg, S.C.) was placed near one edge of the coated scrim and the article was roller around a porous plastic core. The rolls were sealed in foil pouches and allowed to sit so that the width axis of the roll was in the vertical position and the red dye was positioned at the top of the roll. The samples were allowed to sit at roorp temperature for 24 hours. Pooling was determined on a scale of 0–5 with 0 representing no pooling and 5 representing very high pooling of the coated material from the backing. In addition, the distance traveled by the dye down the vertical edge of the roll was used to quantify pooling of the material as was the amount of material left in the pouch upon removal of the roll after one day.

TABLE 25b

| Run Number | Pooling Rating 1–5 | Distance Travelled By Dye (cm) | % Composite[1] Left in Pouch |
|---|---|---|---|
| 1 | 5 | 7.6 | 27.77 |
| 2 | 3 | 6.4 | 5.92 |
| 3 | 1 | 0 | 2.66 |
| 4 | 0.5 | 0 | 1.75 |
| 5 | 0 | 0 | 1.2 |

[1]"% Composite Left in Pouch" was calculated by dividing the weight of the pooled resin by the weight of the coated composite originally present on the tape.

The thickness of an individual layer of coated scrim was measured (using an Ames #2 thickness gauge available from Ames Company, Waltham, Mass.) before curing the roll and compared to the thickness of the uncoated scrim. By subtraction, the thickness of the composite coating was calculated.

Two—6 layer rings of each sample along with a Plaster of Paris control (Cellona) were prepared by dipping the roll for 15 seconds in 23° C. water, rolling the tape around a 5.1 cm diameter mandrel fitted with synthetic stockinet, and molding the ring for several seconds. The 6 layer rings were allowed to sit for 24 hrs. prior to testing for ring strength. The Plaster of Paris control had an average ring strength of 32.9 N/cm.

TABLE 25c

| Run Number | Tape Thickness (cm) | Composite Thickness (cm) | Average Ring Strength (N/cm) |
|---|---|---|---|
| 1 | 0.03 | 0.002 | 30.5 |
| 2 | 0.036 | 0.008 | 34.4 |
| 3 | 0.041 | 0.013 | 34.3 |

TABLE 25c-continued

| Run Number | Tape Thickness (cm) | Composite Thickness (cm) | Average Ring Strength (N/cm) |
|---|---|---|---|
| 4 | 0.046 | 0.018 | 47.4 |
| 5 | 0.053 | 0.025 | 46.2 |

The data illustrates that very strong casting tapes can be produced by coating a heavily filled composite on a lightweight scrim. Runs 3 to 5 exhibited the least amount of pooling, with Runs 4 and 5 being preferred. Notably, Runs 3 to 5 each had a significant amount of "available" composite and were easily molded during application.

Example 26

Composite Viscosities

Several composites having different amounts of filler loading were made to test composite viscosity as a function of volume percent filler. Each sample was made using the ingredients described in Table 26a. The procedure for making Premix A-24 and Premix B-24 is described in Example 24.

TABLE 26a

| Run No. | Premix A-24 (gm) | Premix B-24 (gm) | Sil-35/34 (gm) | $V_f/V_r$ |
|---|---|---|---|---|
| 1 | 112 | 68 | 0 | 0 |
| 2 | 112 | 68 | 5.6 | 0.14 |
| 3 | 112 | 68 | 17.8 | 0.41 |
| 4 | 112 | 68 | 24.5 | 0.57 |
| 5 | 112 | 68 | 31.7 | 0.73 |
| 6 | 112 | 68 | 45 | 1.04 |
| 7 | 56 | 34 | 30 | 1.39 |

Working in a low humidity, constant temperature room, the Sil-35/34 filler was added to a 454 ml glass jar. To this, the respective amounts of Premix A-24 and Premix B-24 were sequentially added. The jar was capped and shaken vigorously for 15 seconds and then stirred with a rubber spatula for about five seconds until a homogenous mixture was obtained. The jar was placed in a 45.6° C. oven for one hour and then allowed to cool to room temperature. The viscosity was measured 7 days after the composite was made. Prior to testing the viscosity of each composite, the composite was heated to 65.5° C. overnight and the sample was stirred vigorously to ensure a homogenous solution of filler and resin. The sample was again allowed to cool to room temperature before testing.

Viscosity was measured using a Rheometrics Dynamic Analyzer II (RDA II) using a parallel plate geometry. All samples were tested under a dry nitrogen environment at 25° C. using dynamic shear mode. Shear rate was varied from 0.1 to 100 rad/s. A strain amplitude of between 2 and 5% was used. Viscosity as a function of filler concentration (at a fixed shear rate) is listed in Table 26b. For the sake of comparison, the Brookfield viscosity of these samples was also measured (see Table 26c). Notably, Runs 6 and 7 had viscosities exceeding the capacity of this apparatus (i.e., greater than 2 million cP).

TABLE 26b

| Run No. | Viscosity (Pa s @ 0.1 rad/s) | Viscosity (Pa s @ 1 rad/s) | Viscosity (Pa s @ 10 rad/s) | Viscosity (Pa s @ 100 rad/s) |
|---|---|---|---|---|
| 1 | 28 | 28 | 35 | 34 |
| 2 | 68 | 68 | 56 | 48 |
| 3 | 190 | 175 | 134 | 112 |
| 4 | 366 | 225 | 177 | 163 |
| 5 | 600 | 367 | 336 | 264 |
| 6 | 4000 | 1430 | 782 | 600 |
| 7 | 36000 | 6000 | 1094 | 1026 |

TABLE 26c

| Run No. | Brookefield Viscosity | | |
|---|---|---|---|
| | Spindle No. | RPM | Viscosity (cP) |
| 1 | 6 | 10 | 52,500 |
| 2 | 6 | 10 | 77,000 |
| 3 | 7 | 10 | 192,000 |
| 4 | 7 | 5 | 378,000 |
| 5 | 7 | 5 | 688,000 |
| 6 | 7 | 5 | >2,000,000 |
| 7 | — | — | — |

Example 27

Surface Smoothness of a Casting Tape

The surface smoothness of a casting tape was measured after the product was molded to show that the composite in this invention can be manipulated such that the casting tape can be taken from a relatively rough surface texture to a smooth surface texture by moving the resin around during the molding of the cast.

A roll of a highly-filled composite coated casting tape was made by adding 30 Grams of Sil-35/34 low density filler; 112 grams of Premix A-24; and 68 Grams of Premix B-24 (heated to 65.5° C.) in order to a 454 ml glass jar. The mixture was shaken vigorously by hand for several seconds and then stirred for several seconds with a rubber spatula. The resin was coated on a cheese cloth scrim as described in Example 24. After coating the cheese cloth scrim with composite the tape was rolled around a 1.905 cm O.D×7.62 cm wide polyethylene core and packaged in an aluminum foil laminate pouch.

Test samples were made using the above casting tape and, for comparison, a plaster of Paris casting tape. Surface smoothness of the products was evaluated, as herein described, after the samples were molded. Flat slabs of each roll were prepared by fan-folding two layers of each sample 25.4 cm long. Each sample was dipped 24° C. water and spread flat on a polyethylene lined counter top. The sample was smoothed by rubbing the tester's finger tips in a circular pattern with very light pressure along the length of the slab until the product was cured to a relatively rigid state. Samples were allowed to sit at ambient conditions before testing for 14 hours.

The cured samples were tested using a Cyberscan laser measuring system manufactured by CyberOptics Corporation, 2505 Kennedy Street NE, Minneapolis, Minn., 55413. Test specimens were attached to a polyester film backing using masking tape to hold the specimens flat during testing. The samples were scanned for surface smoothness over a 5.08 cm using a 0.00254 cm step size and a sensor resolution of PRS 400.

The value reported in Table 27a is the Root Mean Square Value of the average height of the peaks and valleys detected by the laser detector. The RMS value was calculated by breaking the scan into thirds and averaging the RMS of each section of the scan.

TABLE 27a

| Sample ID | Average RMS (cm) |
|---|---|
| Plaster of Paris | 0.004 |
| Highly-filled composite Casting Tape | 0.007 |

As can be seen in the above table, the surface smoothness of the casting tape of the present invention compares very favorably to plaster of Paris. In contrast, a traditional synthetic/fiberglass casting material is very rough. In addition, the smooth casting tape of the present invention can be "autographed" (i.e., written on) just like a plaster of Paris cast.

Example 28

Preparation of Premix A-28: To a 3.8 liter jar under a nitrogen atmosphere was added 2201.6 grams of Isonate 2143L and 2.8 grams of benzoyl chloride. The contents were mixed by shaking and stored at room temperature in a sealed jar.

Preparation of Premix B-28: To a 3.8 liter jar under a nitrogen atmosphere was added 1700 grams Arcol PPG-725 (ARCO Chemical Co., Newtown Square, Pa.), 7.2 grams DB antifoam (Dow Corning Corp., Midland, Mich.), 19.2 grams BHT, and 46.7 grams MEMPE. The contents were mixed by shaking and stored at room temperature in a sealed jar.

The following weighing, mixing and coating steps were done in a dry room (<3% RH). In a 237 ml jar was weighed 10 grams of poly(N-vinyl)pyrrolidone (average $M_w$~360,000, Aldrich Chemical Co., Milwaukee, Wis.). This material had been previously treated by sifting it through a sieve (no. 30, 600 micron openings) and drying it in a vacuum oven (at 90° C. and about 72.7 cm Hg vacuum) for 16 hours. 80.3 g Premix B-28 and 99.7 g Premix A-28 were weighed into the jar and mixed by shaking vigorously.

170 grams of the resulting resin containing dispersed poly(N-vinyl)pyrrolidone was weighed into a one liter jar containing 56.7 grams of Sil-35/34 (Si-Cell brand, Silbrico Corp., Hodgkins, Ill.) which had been dried in a vacuum oven at 120° C. The jar was capped and the contents mixed vigorously by shaking and then by further mixing with a spatula.

The resulting mixture was knife coated onto 28×24 bleached cotton gauze scrim (grade 50 cheesecloth from Twin City Janitor Supply, St. Paul, Minn.) and dried as above. The scrim (7.62 cm by 2.9 m) was placed on the knife coater bed and the knife (bull nose type) was positioned over the scrim at a distance of 0.0254 mm above the bed surface. A portion of the above mixture was poured in front of the knife on top of the scrim and the full length of the scrim was pulled by hand at a slow steady rate under the knife. A total of three pieces of scrim were coated this way with a mean coating weight of 7.6 grams composite mixture per gram of scrim. Each length was loosely rolled onto a perforated, 1.9 cm diameter plastic core, sealed in a foil pouch, and stored for 24 hours at 25° C.

The casting tape was removed from the pouch, dipped in 23° C. water for 10 seconds with squeezing, and wrapped onto a stockinet covered, flexible plastic hand and arm. The material was very easily molded and smoothed out so that overlapping areas could no longer be seen. When cured, the surface of the cast was very smooth. The casting material set in about 3.5 minutes and formed a fully functional (weight-bearing) cast in less than 60 minutes.

Example 29

Surface Smoothness Before and After Molding

Several samples of casting tape were tested to show the difference in surface smoothness after molding the samples. The following samples were evaluated: 7.62 cm wide casting tape as described in Example 24 (Run 1), 10.16 cm wide Carapace XF setting plaster of Paris (Carapace, Inc. Tulsa, Okla.), 7.62 cm wide Scotchcast™ Plus (3M Company, St. Paul, Minn.), and 7.62 cm wide resin impregnated cheesecloth prepared by first mixing 199.4 grams part A-28 and 160.6 grams part B-28 in a 454 ml jar heating at 65.5° C. for 2 hours, cooling 21° C., and coating the cheesecloth as described in Example 28, giving a coating weight of 66.9 grams resin on 7.2 grams cheesecloth (Comparison Run 2).

Each test sample was prepared by fan-folding two layers of the tape (each 25.4 cm long) and submerging in water for 15 seconds. Each sample was placed flat on a polyethylene-lined lab bench top and smoothed by rotating the fingers in a circular direction while applying moderate pressure until the sample was cured.

A piece of cardboard 91.44 cm×91.44 cm was cut with a scissors so that a 30.48 cm×15.25 cm rectangular opening was in the center of one edge of the sheet of cardboard. The cardboard was positioned vertically on a desk top such that the side of the cardboard with the opening was on the desk. The sample of each molded casting tape described above was placed on one side of the opening in the cardboard. Several evaluators sat on the opposite side of the cardboard from the samples, reached their arms through the opening in the cardboard and rubbed their finger tips on the cured molded sample. The evaluators were asked to compare the surface smoothness of the samples with a score of 1 being smoothest and a score of 4 being roughest. The results are listed in Table 29a.

TABLE 29a

| Evaluator Number | Plaster Paris | Run 1 | Scotchcast ™ Plus | Run 2 |
|---|---|---|---|---|
| 1 | 2 | 1 | 3 | 4 |
| 2 | 2 | 1 | 3 | 4 |
| 3 | 3 | 1 | 2 | 4 |
| 4 | 2 | 1 | 3 | 4 |
| 5 | 2 | 1 | 3 | 4 |
| 6 | 2 | 1 | 3 | 4 |
| 7 | 3 | 1 | 2 | 4 |
| 8 | 2 | 1 | 3 | 4 |
| 9 | 2 | 1 | 3 | 4 |
| 10 | 2 | 1 | 3 | 4 |

As can be seen from the above date, the evaluators rated the casting tape of Run 1 as having the smoothest surface.

Example 30

Viscosity of Water Activated Urethane Mixtures on Cheesecloth Scrim

From another roll of the material prepared in Example 28 were taken two 20.3 cm lengths of coated gauze. Each was loosely folded into four layers and protected from moisture until the viscosity after water activation was measured. Viscosity was measured by dipping a four-layer section in 23° C. water for 10 seconds, gently rubbing the surface with a finger to ensure a smooth spread of the resin or composite on the cotton gauze, punching a 2.54 cm diameter section out, and placing this between the two parallel plates of a Rheometrics Dynamic Analyzer II (RDA II) equipped with a 25 mm diameter parallel plate fixture with serrated plates. A compressive force of about 10 grams was used to ensure a good contact with the sample. Steady shear viscosity measurements at a shear rate of $0.2$ $s^{-1}$ were made at 25° C. The first data point used as the initial viscosity of the material was collected 70 seconds after the start of the water dip. This sample had an average viscosity of $1.77 \times 10^4$ Pa s.

A material similar to the material of Example 28 was prepared, but having 30 g Sil-35/34 mixed with 170 g mixture of Premix A-28 and B-28 and being surface coated with K-46 glass bubbles as described in Example 24. When tested as above a viscosity of $2.3 \times 10^4$ Pa s was found. When evaluated as in Example 28, the material could be molded but could not be smoothed out as easily as the Example 28 material.

A material prepared as described in Example 24 was tested as above. Two samples gave a mean viscosity of $1.10 \times 10^4$ Pa s.

A material similar to the material of Example 28 was prepared, but no polyvinylpyrrolidone was used. When tested as above a viscosity of $1.35 \times 10^4$ Pa s was found. When evaluated as in Example 28 the material could not be molded by rubbing, and it stuck to the gloves of the applier.

Example 31

Amount of Composite Material Available for Molding and Smoothing

Approximately 30 cm was removed from a roll of material prepared as described in Example 24 and allowed to cure on a flat table top at 21° C. and 50% relative humidity for four hours. The thickness was found to be about 1.1 mm using an Ames 202 micrometer (Ames, Waltham, Mass.). Using a razor blade, a section approximately 1 cm×3 cm was cut from the sample in the width direction. This was mounted with the cut edge up and examined in a scanning electron microscope at 100x. The cotton yarn cross sections (about 180 microns in diameter) were found to be surrounded by approximately 150 to 300 microns of composite material. Thus, a large amount of composite material was available for molding and smoothing the material.

Example 32

Use of Amoco RFX Spunbonded Nonwoven as the Scrim

A 10.16 cm wide by 3 m long strip of 10 g/ml RFX spunbonded nonwoven fabric (AMOCO Fabrics and Fibers Company, Atlanta, Ga.) was coated as described in Example 24, but at a pull rate of about 2.54 cm/sec. After storage in a foil pouch at room temperature for 10 days, the roll was rerolled very loosely onto another porous plastic core and sealed in a foil pouch in a room kept at less than 3% relative humidity. After 24 hours, the coated RFX casting tape was evaluated as described in Example 28. The material conformed well to the plastic hand and arm during wrapping and was very easy to hand mold and smooth out; so that any overlap areas could no longer be seen, the surface was smooth, and the resulting cast followed the shape of the hand and arm. The material set in about 3 minutes and was a rigid cast in 30 minutes.

What is claimed is:

1. A method of making a light-weight orthopedic casting article, comprising the steps of:

mixing a polyisocyanate compound, a reactive hydrogen compound, and a filler to form a composite mixture;

coating the composite mixture on a light-weight scrim while the polyisocyanate compound and the reactive hydrogen compound are at most only partially reacted and while the composite mixture's viscosity is low enough so that the composite mixture can be spread out on the scrim to form a coated scrim; and then allowing the polyisocyanate compound and the reactive hydrogen compound to further react, thereby forming a water-curable isocyanate-functional prepolymer and thereby increasing the viscosity of the composite mixture to an extent that the composite mixture resists pooling during storage, wherein the ratio of the volume of the filler divided by the volume of the water-curable isocyanate-functional prepolymer is greater than 0.4.

2. The method according to claim 1, further comprising the step of:

dusting additional amounts of the filler onto the surfaces of the coated scrim.

3. The method of claim 1, wherein the ratio of the volume of the filler divided by the volume of the water-curable isocyanate-functional prepolymer is greater than 0.8, and wherein the scrim has a basis weight less than 30 g/m$^2$ and is selected from the group consisting of cotton and polymeric knit, wovens and non-wovens.

4. The method of claim 1, wherein the filler is selected from the group consisting of glass and ceramic bubbles having an average particle diameter between 5 and 500 μm, and a specific gravity less than about 2, wherein the article is in the form of an orthopedic casting tape or splint.

5. The method of claim 4, wherein the article is in the form of a casting tape which, when cured, provides an exterior surface which is as smooth as a plaster of Paris cast.

6. The method according to claim 1, wherein the coating step comprises the steps of: pouring the composite mixture onto the scrim and then pulling the scrim through the gap of a knife coater.

7. The method according to claim 6, wherein the coated scrim is then processed further by feeding the scrim past a horizontal roller that is immersed in a reservoir containing additional filler.

8. The method according to claim 7, further comprising the step of:

dusting additional amounts of the filler onto the surfaces of the coated scrim.

9. The method according to claim 1, wherein the mixing step is performed in a dry environment having less than 5% relative humidity.

10. The method according to claim 1, wherein the ratio of the volume of the filler divided by the volume of the water-curable isocyanate-functional prepolymer is greater than 0.6.

11. The method according to claim 1, wherein the water-curable isocyanate-functional prepolymer has an NCO/OH ratio greater than 2.5.

12. The method according to claim 1, wherein the filler has a specific gravity less than about 3.

13. A method of making a light-weight orthopedic casting article, comprising the steps of:

mixing a polyisocyanate compound, a reactive hydrogen compound, a volatile solvent and a filler to form a composite mixture;

coating the composite mixture on a light-weight scrim while the composite mixture's viscosity is low enough so that the composite mixture can be spread out on the scrim; and then removing the volatile solvent, thereby increasing the viscosity of the composite mixture to an extent that the composite mixture resists pooling during storage, wherein the volume of the filler divided by the volume of the polyisocyanate and reactive hydrogen compounds is greater than 0.4.

14. The method according to claim 13, further comprising the step of:

dusting additional amounts of the filler onto the surfaces of the coated scrim.

15. The method of claim 13, wherein the ratio of the volume of the filler divided by the volume of the polyisocyanate and reactive hydrogen compounds is greater than 0.8, and wherein the scrim has a basis weight less than 30 g/m$^2$ and is selected from the group consisting of cotton and polymeric knit, wovens and non-wovens.

16. The method of claim 13, wherein the filler is selected from the group consisting of glass and ceramic bubbles having an average particle diameter between 5 and 500 μm, and a specific gravity less than about 2.

17. A method of making a light-weight orthopedic casting article, comprising the steps of:

mixing a water-curable resin and a filler to form a composite mixture; and applying the composite mixture on a light-weight scrim, wherein the ratio of the volume of the filler divided by the volume of the water-curable resin is greater than 0.4.

18. The method of claim 17, wherein the scrim has a basis weight less than 30 g/m$^2$ and is selected from the group consisting of cotton and polymeric knit, wovens and non-wovens.

19. The method of claim 17, wherein the filler is selected from the group consisting of glass and ceramic bubbles having an average particle diameter between 5 and 500 μm, and a specific gravity less than about 2.

* * * * *